US008343923B2

(12) United States Patent
Long et al.

(10) Patent No.: US 8,343,923 B2
(45) Date of Patent: Jan. 1, 2013

(54) USE OF NOTCH SIGNALING REGULATORS FOR MODULATING OSTEOGENESIS

(75) Inventors: Fanxin Long, St. Louis, MO (US); Matthew J. Hilton, St. Louis, MO (US); Xiaolin Tu, St. Louis, MO (US)

(73) Assignee: Washington University, St. Louis, MO (US)

( * ) Notice: Subject to any disclaimer, the term of this patent is extended or adjusted under 35 U.S.C. 154(b) by 195 days.

(21) Appl. No.: 12/268,268

(22) Filed: Nov. 10, 2008

(65) Prior Publication Data

US 2009/0156510 A1 Jun. 18, 2009

Related U.S. Application Data

(60) Provisional application No. 60/986,755, filed on Nov. 9, 2007.

(51) Int. Cl.
*A61K 38/00* (2006.01)
*A61P 19/08* (2006.01)
*C12N 5/00* (2006.01)

(52) U.S. Cl. ...................................... 514/16.7; 435/375

(58) Field of Classification Search .................. None
See application file for complete search history.

(56) References Cited

U.S. PATENT DOCUMENTS

| | | | |
|---|---|---|---|
| 5,480,439 A | 1/1996 | Bisek et al. | |
| 5,572,998 A | 11/1996 | ONeill et al. | |
| 5,643,736 A | 7/1997 | Bruder et al. | |
| 5,712,892 A | 1/1998 | Weil et al. | |
| 5,715,820 A | 2/1998 | Stein et al. | |
| 5,745,544 A | 4/1998 | Mazess | |
| 5,749,363 A | 5/1998 | Ishii et al. | |
| 5,778,045 A | 7/1998 | von Stetten et al. | |
| 5,782,763 A | 7/1998 | Bianco et al. | |
| 5,817,020 A | 10/1998 | Ishii et al. | |
| 5,852,647 A | 12/1998 | Schick et al. | |
| 5,891,033 A | 4/1999 | ONeill et al. | |
| 5,898,753 A | 4/1999 | Schick et al. | |
| 6,058,157 A | 5/2000 | Christiansen et al. | |
| 6,102,567 A | 8/2000 | Cabral et al. | |
| 6,213,934 B1 | 4/2001 | Bianco et al. | |
| 6,230,036 B1 | 5/2001 | ONeill et al. | |
| 6,246,745 B1 | 6/2001 | Bi et al. | |
| 6,302,582 B1 | 10/2001 | Nord et al. | |
| 6,320,931 B1 | 11/2001 | Arnold | |
| 6,405,068 B1 | 6/2002 | Pfander et al. | |
| 6,436,042 B1 | 8/2002 | Cadossi et al. | |
| 2006/0264380 A1* | 11/2006 | Hellstrom et al. ............... 514/19 |

FOREIGN PATENT DOCUMENTS

WO WO 2005/008250 * 1/2005

OTHER PUBLICATIONS

Isefuku et al. Gentamicin May Have an Adverse Effect on Osteogenesis. Journal of Orthopaedic Trauma. 2003. vol. 17. No1. 3, pp. 212-216.*

Artavanis-Tsakonas, et al, Notch signaling: cell fate control and signal integration in development, Science, 1999, pp. 770-776, vol. 284, No. 5415.
Bianco, P., et al, Bone Marrow Stromal Stem Cells: Nature, Biology, and Potential Applications, Stem Cells, 2001, pp. 180-192, vol. 19.
Chiba, Shigeru, Concise Review: Notch Signaling in Stern Cell Systems, Stem Cells, 2006, pp. 2437-2447, vol. 24.
Conlon, et al, Notch1 is required for the coordinate segmentation of somites, Development, 1995, pp. 1533-1545, vol. 121.
Deregowski, et al, Notch 1 Overexpression Inhibits Osteoblastogenesis by Suppressing Wnt/β-Catenin but Not Bone Morphogenetic Protein Signaling, J. Biological Chem., 2006, pp. 6203-6210, vol. 281, No. 10.
Domenga, et al, Notch3 is required for arterial identity and maturation of vascular smooth muscle cells, Genes Dev., 2004, pp. 2730-2735, vol. 18.
Donoviel, et al, Mice Lacking both presenilin genes exhibit early embryonic patterning defects, Genes Dev., 1999, pp. 2801-2810, vol. 13.
Duarte, et al, Dosage-sensitive requirement for mouse Dll4 in artery development, Genes Dev., 2004, pp. 2474-2478, vol. 18.
Ducy et al, Osf2/Cbfa1: a transcriptional activator of osteoblast differentiation, Cell, 1997, pp. 747-754, vol. 89, No. 5.
Dunwoodie et al, Axial skeletal defects caused by mutation in the spondylocostal dysplasia/pudgy gene Dll3 are associated with disruption of the segmentation clock within the presomitic mesoderm, Development, 2002, pp. 1795-1806, vol. 129.
Gale, et al, Haploinsufficiency of delta-like 4 ligand results in embryonic lethality due to major defects in arterial and vascular development, PNAS, 2004, pp. 15949-15954, vol. 101, No. 45.
Hamada, et al, Mutation in ankyrin repeats of the mouse Notch2 gene induces early embryonic lethality, Development, 1999, pp. 3415-3424, vol. 126.
Herreman, et al, Presenilin 2 deficiency causes a mild pulmonary phenotype and no changes in amyloid precursor protein processing but enhances the embryonic lethal phontype of presenilin 1 deficiency, PNAS, 1999, pp. 11872-11877, vol. 96, No. 21.
Hessle et al, Tissue-nonspecific alkaline phosphatase and plasma cell membrane glycoprotein-1 are central antagonistic regulators of bone mineralization, PNAS, 2002, pp. 9445-9449, vol. 99, No. 14.
Hilton, et al, Ihh controls cartilage development by antagonizing Gli3, but requires additional effectors to regulate osteoblast and vascular development, Development, 2005, pp. 4339-4351, vol. 132.
Honjo, T., The shortest path from the surface to the nucleus: RBP-J kappa/Su (H) transcription factor, Genes Cells, 1996, pp. 1-9, vol. 1, No. 1.
Hrabe De Angelis, et al, Maintenance of somite borders in mice requires the Delta homologue Dll1, Nature, 1997, pp. 717-721, vol. 386.
Jiang, et al, Defects in limb, craniofacial, and thymic development in Jagged2 mutant mice, Genes Dev., 1998, pp. 1046-1057, vol. 12.
Karsenty, et al, Reaching a genetic and molecular understanding of skeletal development, Dev Cell, 2002, pp. 389-406, vol. 2, No. 4.
Kinoshita et al. Direct visualization of the gamma secretase-generated carboxyl-terminal domain of the amyloid precursor protein: association with Fe65 and translocation to the nucleus, J Neurochem., 2002, pp. 839-847, vol. 82, No. 4.

(Continued)

*Primary Examiner* — Marcela M Cordero Garcia
(74) *Attorney, Agent, or Firm* — Polsinelli Shughart PC

(57) ABSTRACT

The present invention provides methods of treating osteoporosis and other bone disorders by inhibiting Notch signaling.

12 Claims, 30 Drawing Sheets

OTHER PUBLICATIONS

Köhler, et al, Continuous cultures of fused cells secreting antibody of predefined specificity, Nature, 1975, pp. 495-497, vol. 256, No. 5517.

Komori et al., Targeted disruption of Cbfa1 results in a complete lack of bone formation owing to maturational arrest of osteoblasts, Cell, 1997, pp. 755-764, vol. 89, No. 5.

Kopan et al, A common enzyme connects Notch signaling and Alzheimer's disease, Genes Dev., 2000, pp. 2799-2806, vol. 14.

Krebs, et al, Notch signaling is essential for vascular morphogenesis in mice, Genes Dev., 2000, pp. 1343-1352, vol. 14.

Kuznetsov, et al, The interplay of osteogenesis and hematopoiesis: expression of a constitutively active PTH/PTHrP receptor in osteogenic cells perturbs the establishment of hematopoiesis in bone and of skeletal stem cells in the bone marrow, J. Cell Biol., 2004, pp. 1113-1122, vol. 167, No. 6.

Logan et al, Expression of Cre Recombinase in the developing mouse limb bud driven by a Prxl enhancer, Genesis, 2002, pp. 77-80, vol. 33, No. 2.

McCright, et al, Generation of new Notch2 mutant alleles, Genesis, 2006, pp. 29-33, vol. 44, No. 1.

Miao, et al, Osteoblast-derived PTHrP is a potent endogenous bone anabolic agent that modifies the therapeutic efficacy of administered PTH 1-34, J. Clin. Invest., 2005, pp. 2402-2411, vol. 115, No. 9.

Nakashima et al, The novel zinc finger-containing transcription factor osterix is required for osteoblast differentiation and bone formation, Cell, 2002, pp. 17-29, vol. 108, No. 1.

Olsen et al, Bone Development, Annu. Rev. Cell. Dev. Biol., pp. 191-220, 2000, vol. 16.

Owen, et al, Stromel stem cells: marrow-derived osteogenic precursors, Ciba Found Symp., 1988, pp. 42-60, vol. 136.

Pan et al, Gamma-secretase functions through Notch signaling to maintain skin appendages but is not required for their patterning or initial morphogenesis, Dev. Cell, 2004, pp. 731-743, vol. 7, No. 5.

Pan et al, Notch1 and 2 cooperate in limb ectoderm to receive an early Jagged2 signal regulating interdigital apoptosis, Dev. Biol., 2005, pp. 472-482, vol. 286, No. 2.

Ricciardelli et al, Development and characterization of primary cultures of smooth muscle cells from the fibrmuscular stroma of the guinea pig prostate, In Vitro Cell Dev. Biol., 1989, pp. 1016-1024, vol. 25, No. 11.

Schroeter, et al, Notch-1 signaling requires ligand-induced proteolytic release of intracellular domain, Nature, 1998, pp. 382-386, vol. 393, No. 6683.

Shen, et al, Skeletal and CNS defects in Presenilin-1-deficient mice, Cell, 1997, pp. 629-639, vol. 89, No. 4.

Swiatek, et al, Notch1 is essential for postimplantation development in mice, Genes Dev., 1994, pp. 707-719, vol. 8.

Tezuka, et al, Stimulation of osteoblastic cell differentiation by Notch, J. Bone Miner. Res., 2002, pp. 231-239, vol. 17, No. 2.

Tu et al, Noncanonical Wnt Signaling through G Protein-Linked PKCδ Activation Promotes Bone Formation, Dev Cell, 2007, pp. 113-127, vol. 12, No. 1.

Wong, et al, Presenillin 1 is required for Notch1 and Dll1 expression in the paraxial mesoderm, Nature, 1997, pp. 288-292, vol. 387, No. 6630.

Xue et al, Embryonic lethality and vascular defects in mice lacking the Notch ligand Jagged1, Human Molecular Genetics, 1999, pp. 723-730, vol. 8, No. 5.

Yu, et al, APP processing and synaptic plasticity in presenillin-1 conditional knockout mice, Neuron, 2001, pp. 713-726, vol. 31, No. 5.

Zamurovic, et al, Coordinated Activation of Notch, Wnt, and Transforming Growth Factor-β Signaling Pathways in Bone Morphogenic Protein 2-induced Osteogenesis, J. Biol. Chem., 2004, pp. 37704-37715, vol. 279, No. 36.

\* cited by examiner

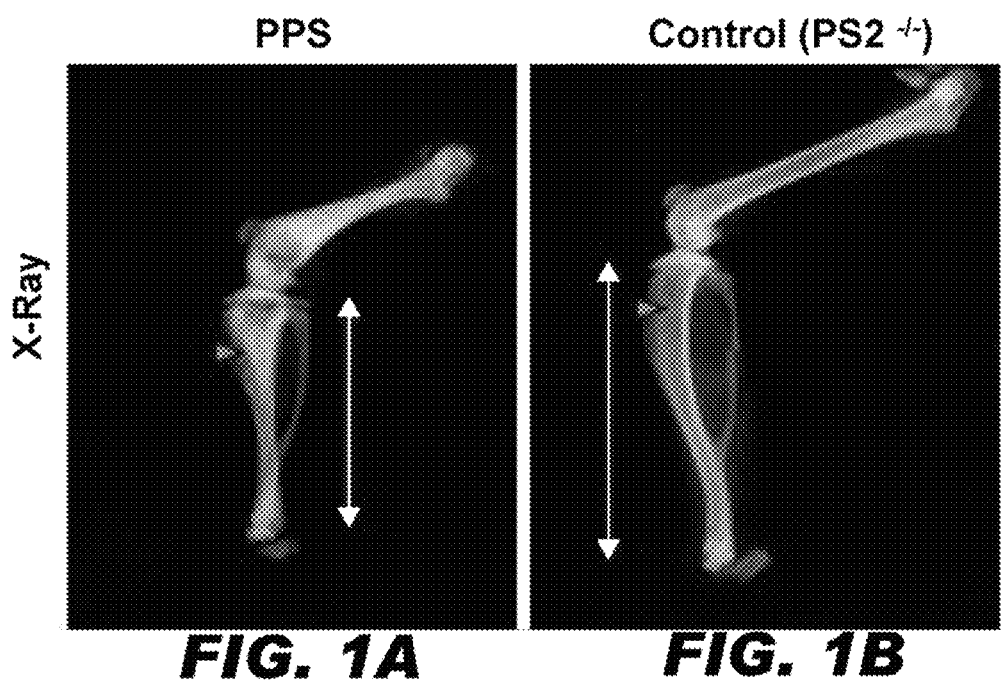
FIG. 1A     FIG. 1B
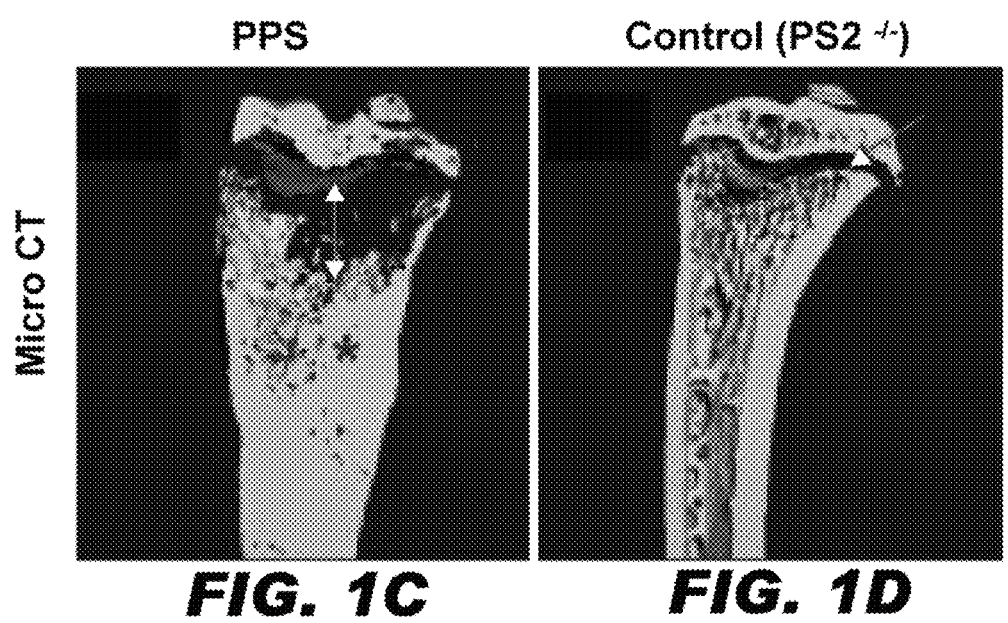
FIG. 1C     FIG. 1D

Control (PS2 -/-)

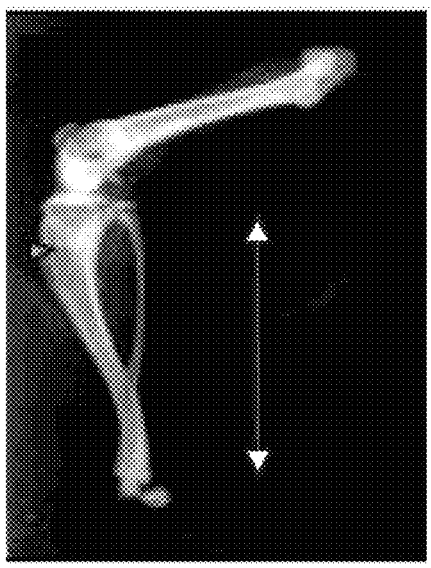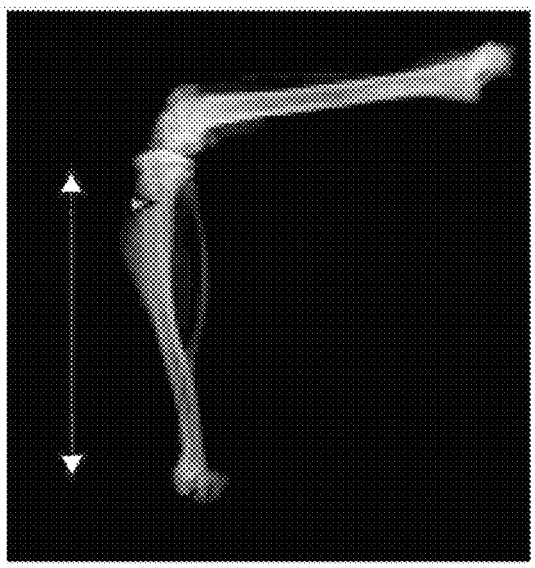
FIG. 3A      FIG. 3B
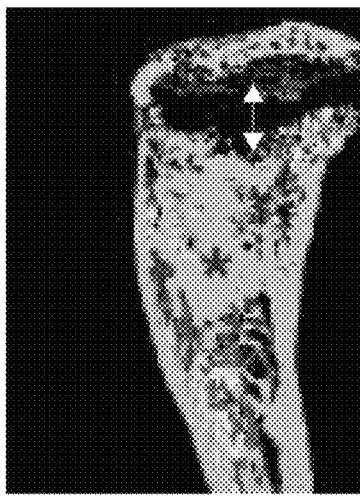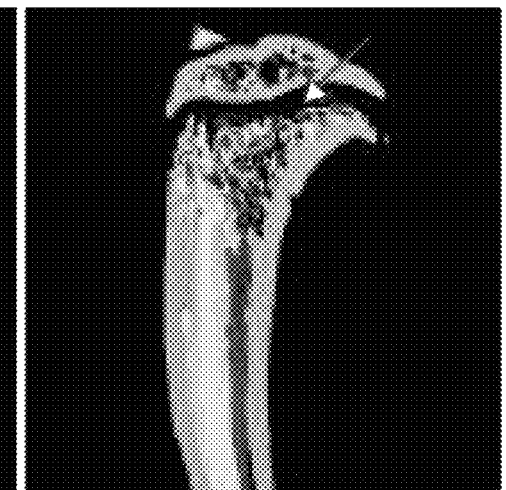
FIG. 3C      FIG. 3D

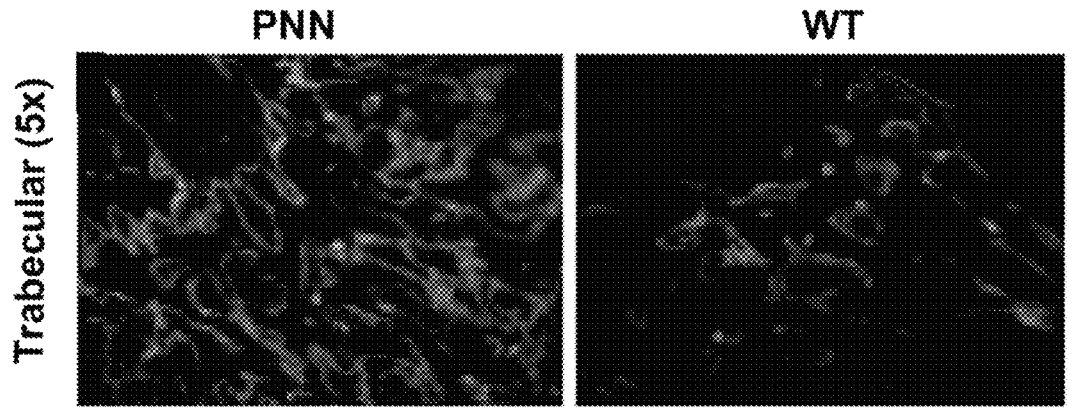
FIG. 3R     FIG. 3S
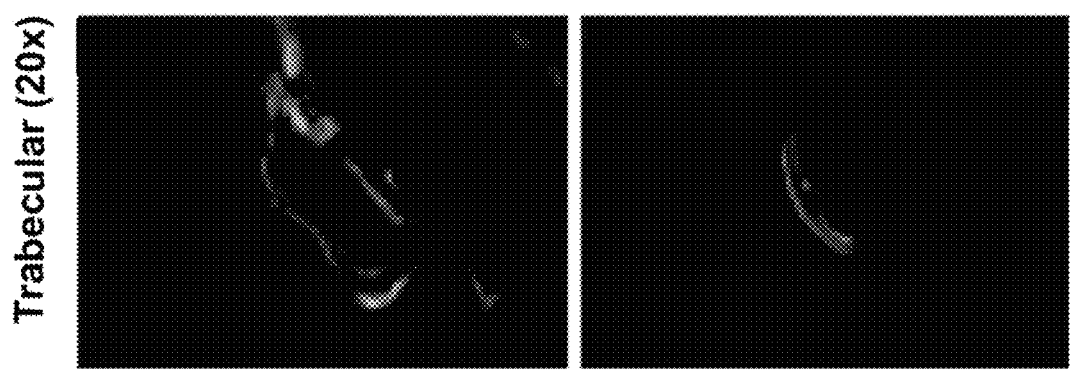
FIG. 3T     FIG. 3U
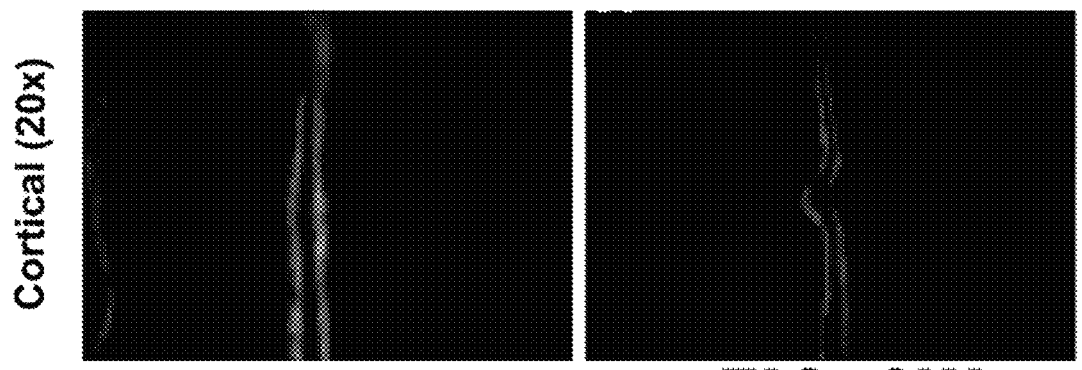
FIG. 3V     FIG. 3W

E18.5 Control | E18.5 PPS
FIG. 4A Ihh  FIG. 4G 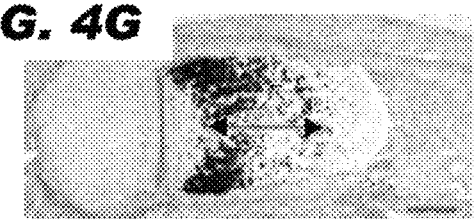
FIG. 4B ColX  FIG. 4H 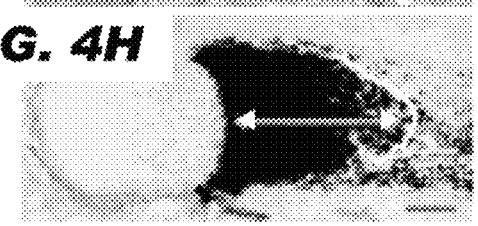
FIG. 4C MMP13  FIG. 4I 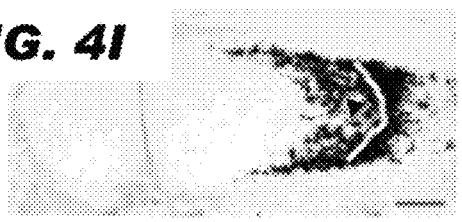
FIG. 4D H & E 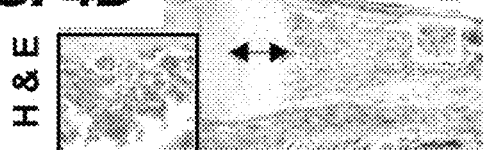 FIG. 4J 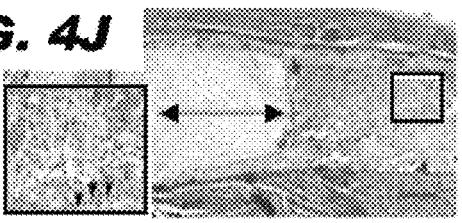
FIG. 4E BSP 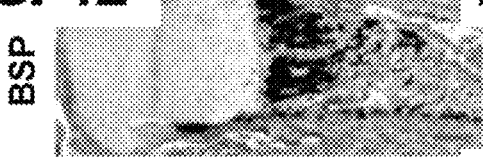 FIG. 4K 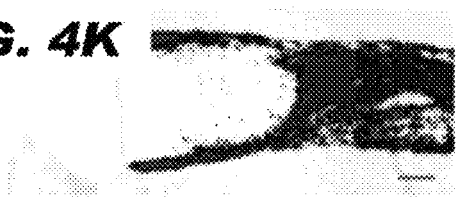
FIG. 4F TRAP 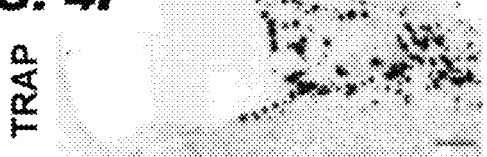 FIG. 4L 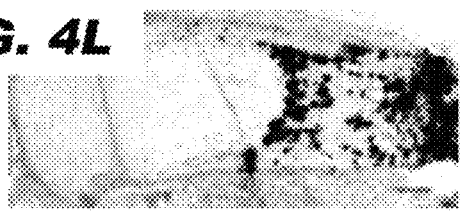

E14.5 Control  E14.5 PPS
FIG. 4M Ihh 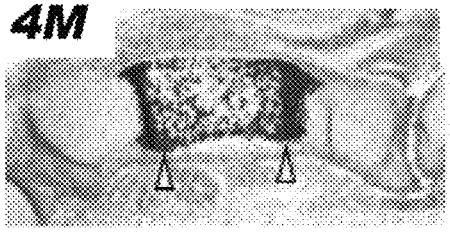  FIG. 4Q 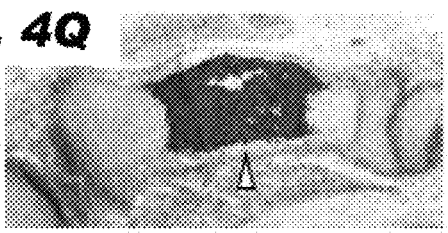
FIG. 4N ColX 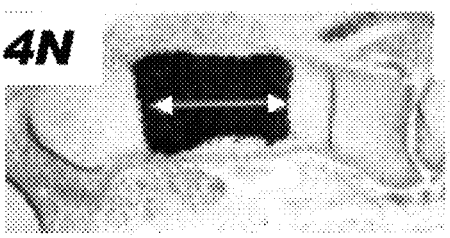  FIG. 4R 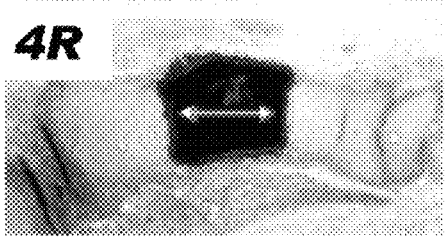
FIG. 4O MMP13 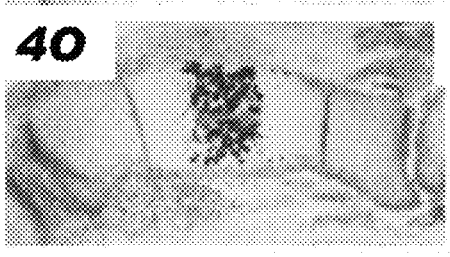  FIG. 4S 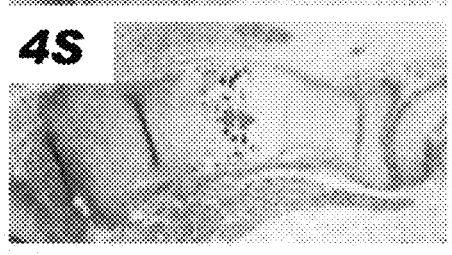
FIG. 4P H & E 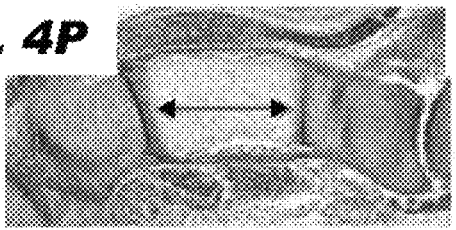  FIG. 4T 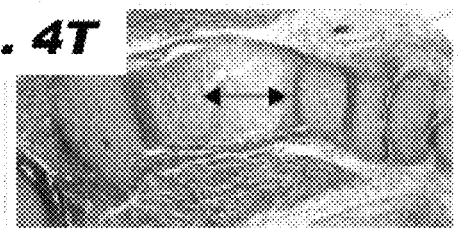

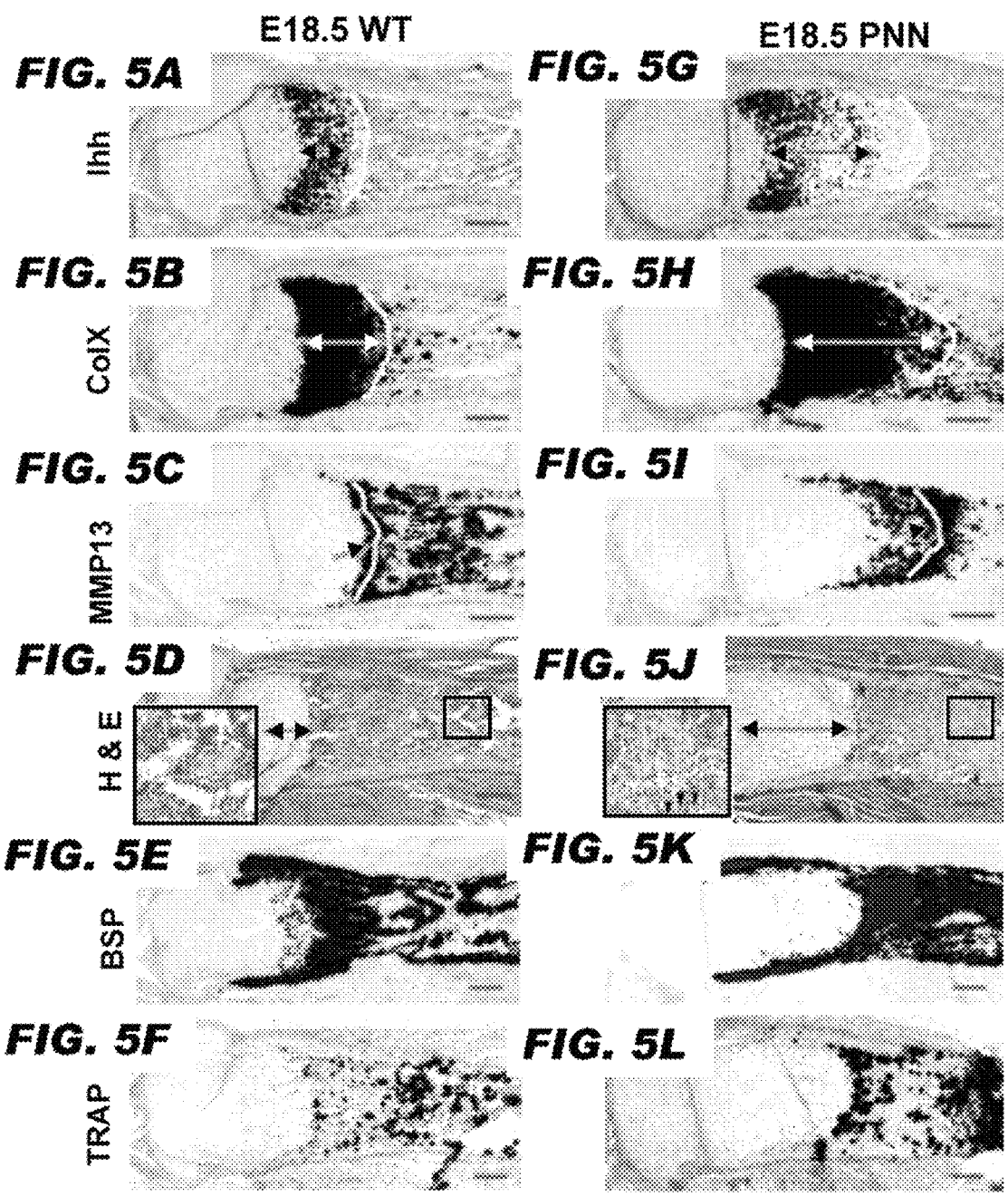

E14.5 WT
FIG. 5M Ihh
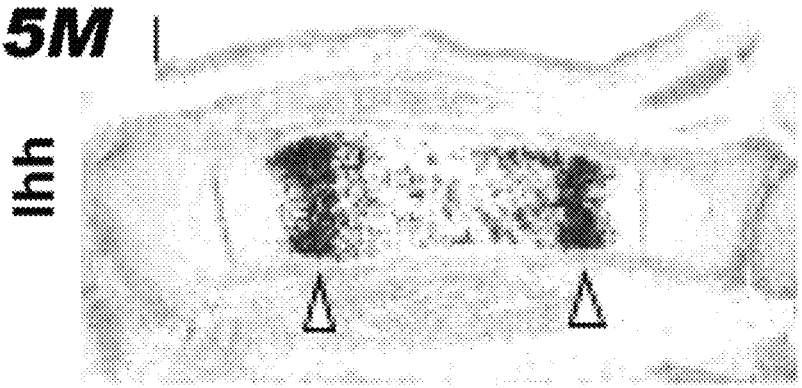
FIG. 5N ColX
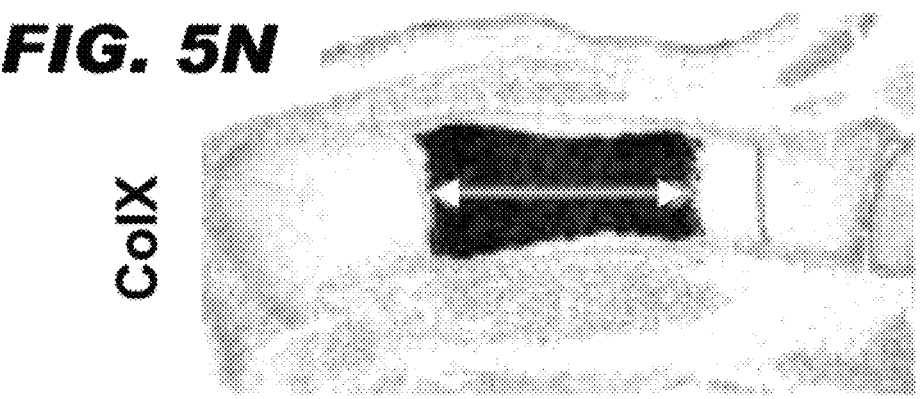
FIG. 5O MMP13
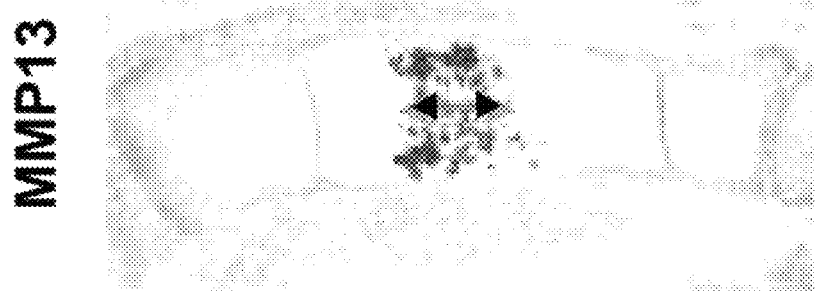
FIG. 5P H & E
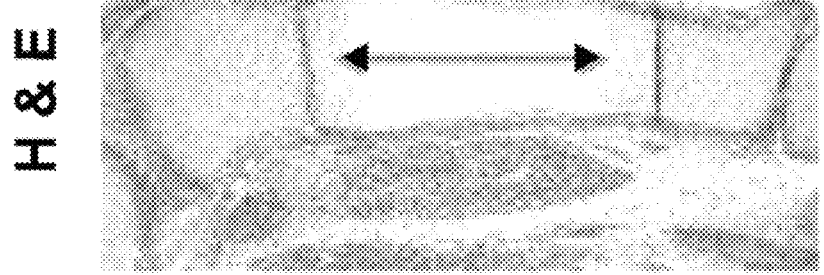

E14.5 PNN
FIG. 5R  Ihh
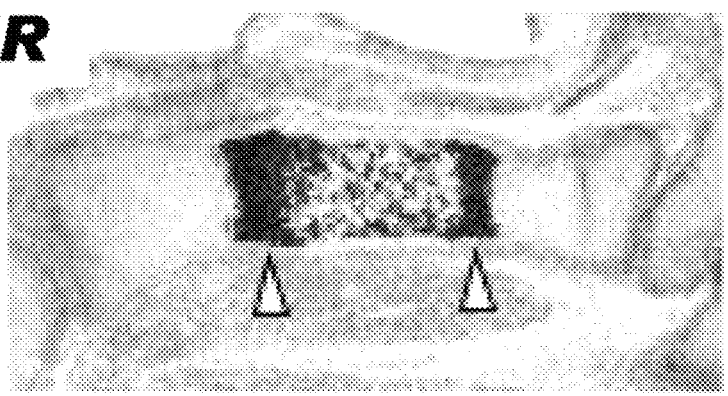
FIG. 5S  ColX
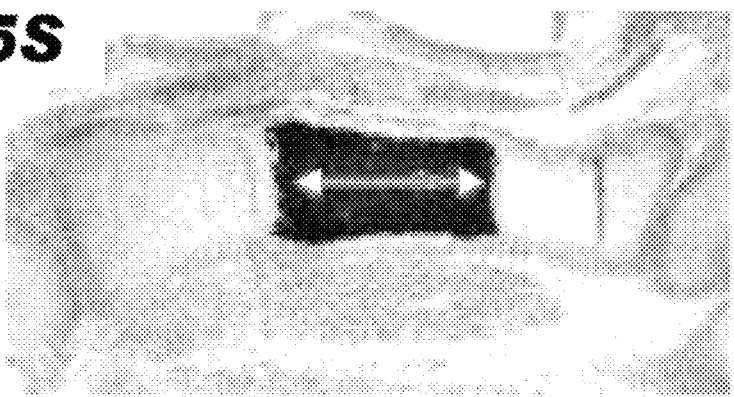
FIG. 5T  MMP13
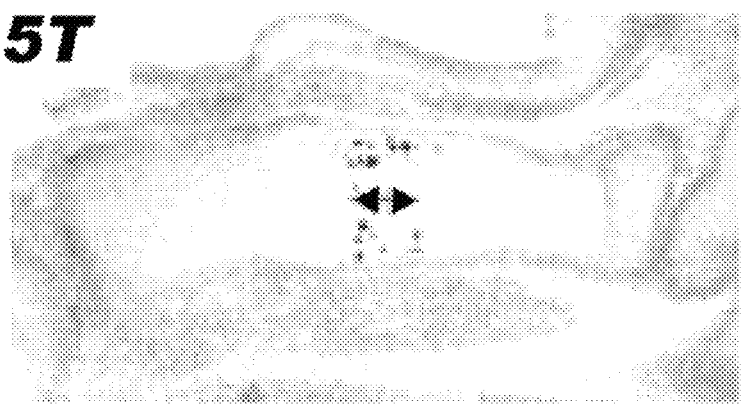
FIG. 5U  H & E
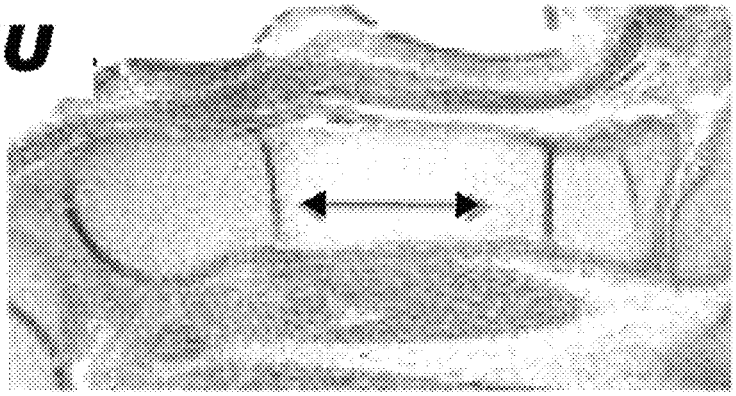

E18.5 H & E (Tibia)    Marrow Cavity (20x)
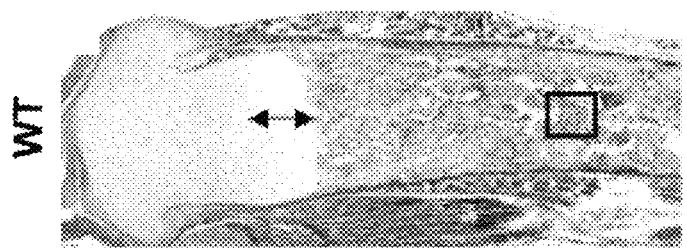 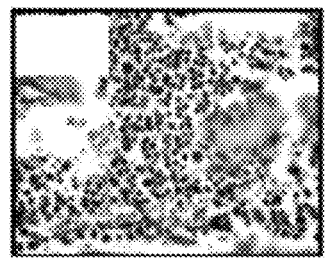
FIG. 6A — FIG. 6B
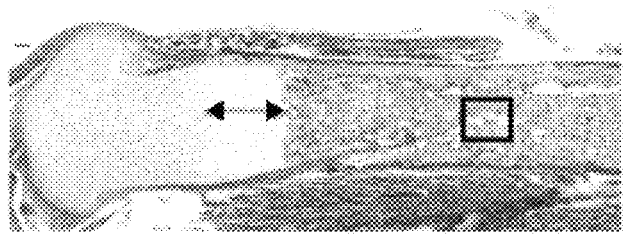 
FIG. 6C — FIG. 6D
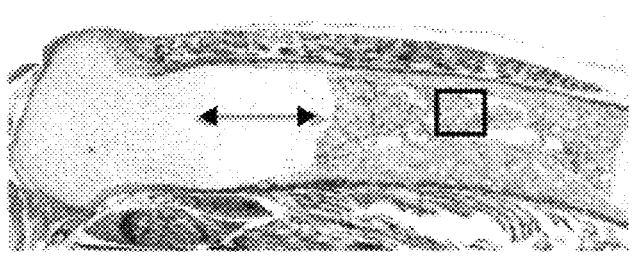 
FIG. 6E — FIG. 6F
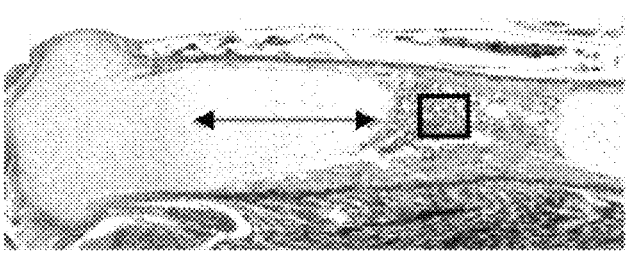 
FIG. 6G — FIG. 6H

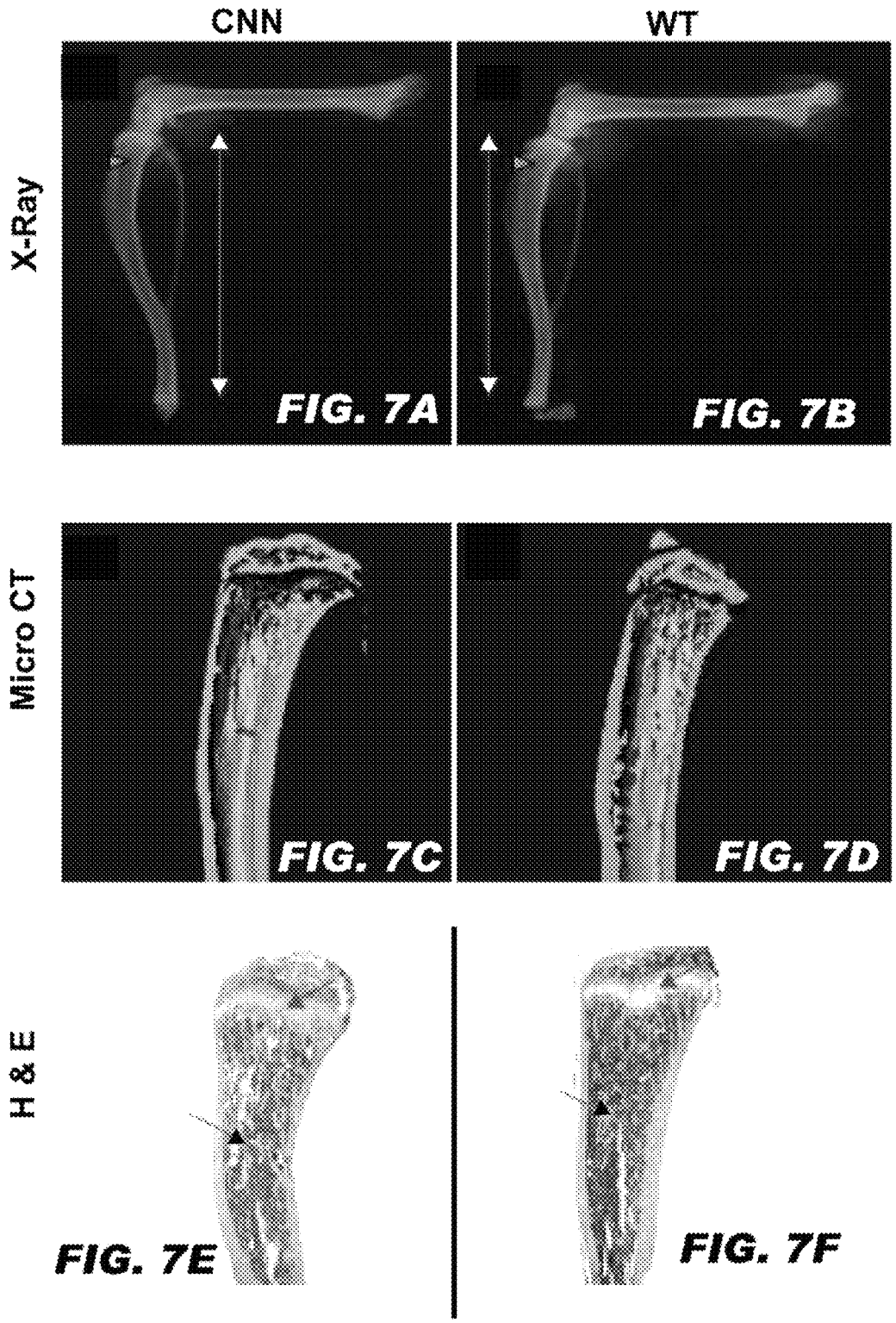

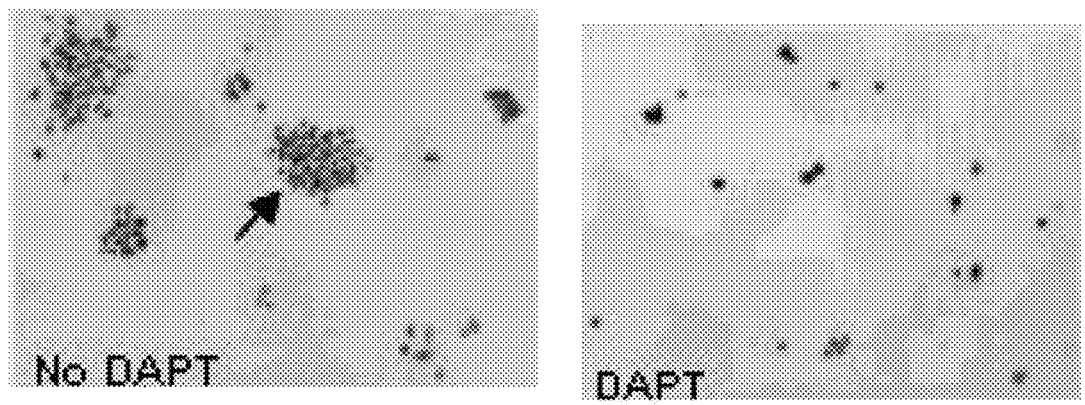
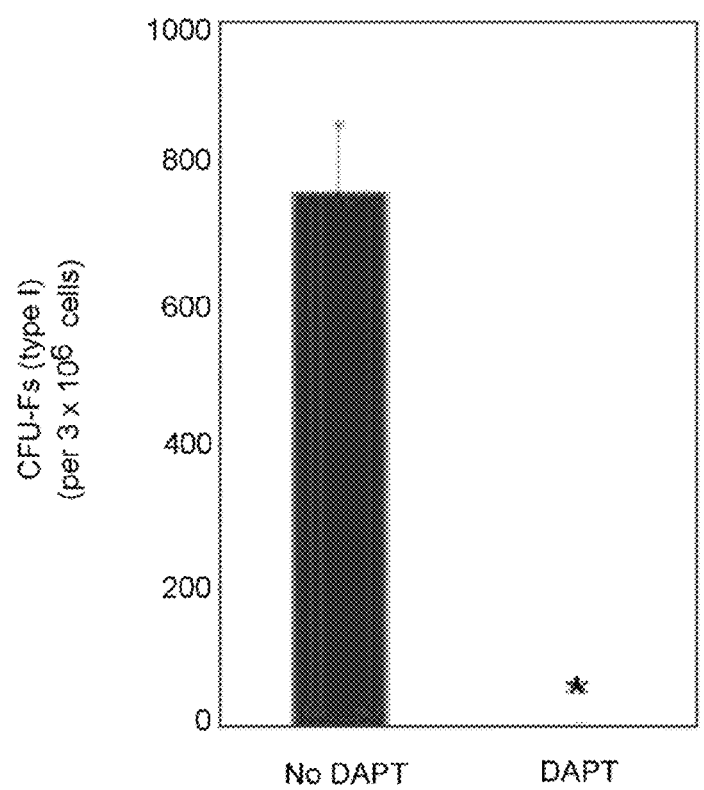
FIG. 8E

No DAPT          DAPT

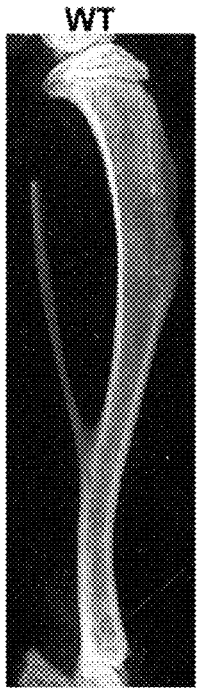
FIG. 10A
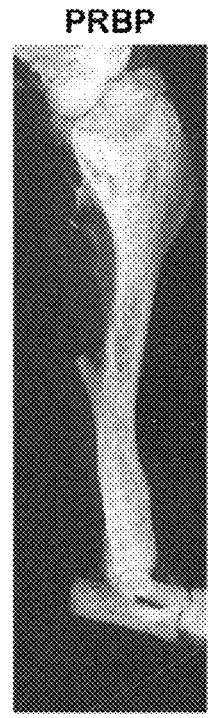
FIG. 10B
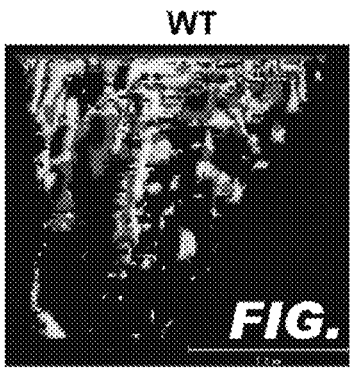
FIG. 10C1
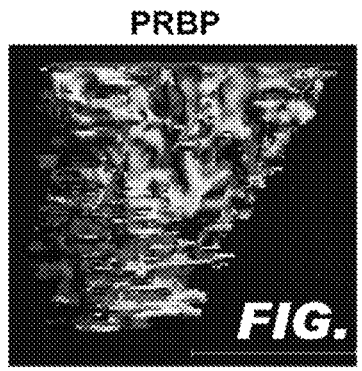
FIG. 10D1
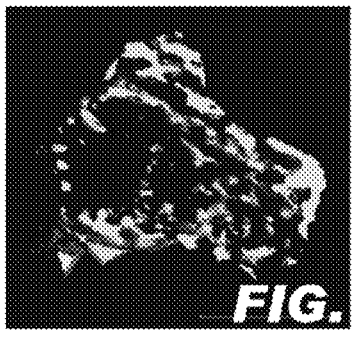
FIG. 10C2
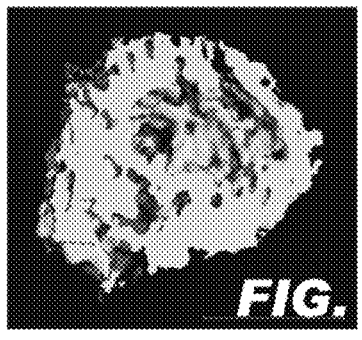
FIG. 10D2

USE OF NOTCH SIGNALING REGULATORS FOR MODULATING OSTEOGENESIS

CROSS REFERENCE TO RELATED APPLICATIONS

This application claims the priority of U.S. provisional patent No. 60/986,755, filed on Nov. 9, 2007, which is hereby incorporated by reference in its entirety.

GOVERNMENTAL RIGHTS

This invention was made with government support under NIH grant numbers DK065789 and 5T32AR07033. The government has certain rights in the invention.

FIELD OF THE INVENTION

The present invention generally relates to a method of inhibiting bone loss.

BACKGROUND OF THE INVENTION

Bone undergoes continuous remodeling through interactive cycles of bone formation and resorption (bone turnover). Approximately 10% of the bone mass is removed and replaced in an average adult over the course of one year. Osteoclasts and osteoblasts, the major differentiated cells of bone, mediate the remodeling process. Typically, bone resorption is a rapid process that is mediated by osteoclasts, which are cells formed by mononuclear phagocytic precursor cells located at bone remodeling sites. The bone resorption process is followed by the appearance of osteoblasts (bone forming cells), which form bone slowly to replace the lost bone. The fact that completion of this process normally leads to balanced replacement and renewal of bone indicates that the molecular signals and events that influence bone remodeling are tightly controlled.

The mechanism of bone loss is not understood, but in general, bone loss associated disorders arise from an imbalance in the formation of new healthy bone and the resorption of old bone, skewed toward a net loss of bone tissue. This bone loss includes a decrease in both mineral content and protein matrix components of the bone, and leads to an increased fracture rate of the femoral bones and bones in the forearm and vertebrae predominantly. These fractures, in turn, lead to an increase to general morbidity, a marked loss of stature and mobility, and in many cases, an increase in mortality resulting from complications.

Several bone growth disorders are known that cause an imbalance in the bone remodeling cycle. Chief among these are metabolic bone diseases, such as osteoporosis, osteomalacia/rickets, chronic renal failure and hyperparathyroidism, which result in abnormal or excessive loss of bone mass (osteopenia), osteogenesis, osteopetrosis, and Paget's disease. Further, bone loss and a decrease in bone mineralization is often associated with therapies used to treat non-bone associated conditions such as HIV/AIDS, autoimmune disease, epilepsy, and juvenile rheumatoid arthritis, increasing the chances of bone fracture in the recipient.

Improvements in existing therapies and development of new treatments are needed to combat bone loss and promote bone growth. For instance, in the common bone ailment osteoporosis, skeletal mineral losses are in the range of 50% below peak bone mass, which occurs at approximately age 30. Seen from the perspective of correcting the deficit in bone mineral, complete reversal of this 50% loss would require a 100% increase in bone mass. Thus, seen from this perspective, the 2-8% increases in bone mineral density resulting from anti-resorptive therapy may be clinically significant and beneficial, but leaves a lot of room for improvement. Since the use of anti-resorptives to prevent bone loss does not result in new bone production, the ultimate effectiveness of anti-resorptives in quantitative terms is limited. These considerations emphasize the need for the development of pharmaceutical mechanisms to produce new bone.

SUMMARY OF THE INVENTION

One aspect of the invention encompasses a method for promoting osteogenesis in a subject, the method comprising administering a Notch signaling inhibitor to a subject in need of osteogenesis.

Another aspect of the invention encompasses a method for treating a bone disorder, the method comprising contacting a mammalian cell with a Notch signaling inhibitor whereby the mammalian cell differentiates into a cell of an osteoblast lineage.

Other aspects and iterations of the invention are described more thoroughly below.

BRIEF DESCRIPTION OF THE DRAWINGS

FIG. 4 shows molecular and histological analyses in PPS and wild type (WT) embryos. In situ hybridization on adjacent longitudinal sections through the tibia from E18.5 littermates is shown in FIGS. 4A-4C, 4G-4I, 4E-4F, 4K-4L. (Double-headed arrows denote length of expression domain; yellow contours demarcate chondro-osseous junction; arrows point to last row of hypertrophic chondrocytes) Medial longitudinal sections through the tibia of E18.5 littermates were stained with H&E (FIGS. 4D and 4J). Boxed regions are shown at high magnification as insets. (Double-headed arrows: length of hypertrophic zone) In situ hybridization for Indian Hedgehog (Ihh) was done on adjacent longitudinal sections through the tibia from E14.5 littermates (FIG. 4M-4O and 4Q-4S). Yellow arrowheads denote major expression domains of Ihh. (Doubleheaded arrows: lengths of expression domains) Medial longitudinal sections through the tibia of E14.5 littermates were stained with H&E (FIGS. 4P and 4T). (Double-headed arrows: length of hypertrophic zone)

FIG. 6 shows histology of longitudinal sections through the tibia of E18.5 embryos with various combinations of Notch1 and Notch2 alleles with samples from wild type (FIGS. 6A and 6B), Prx1Cre; N1$^{c/c}$; N2$^{c/+}$ (FIGS. 6C and 6D), Prx1Cre; N1$^{c/+}$; N2$^{c/c}$ (FIGS. 6E and 6F), and Prx1Cre; N1$^{c/c}$; N2$^{c/c}$ (FIG. 6G-6H). Double-headed arrows denote the length of the hypertrophic zone. FIGS. 6B, 6D, 6F, and 6H show the higher magnification of boxed areas in FIGS. 6A, 6C, 6E, and 6G, respectively. (M: marrow).

FIG. 8 demonstrates notch regulation of bone marrow mesenchymal progenitors. FIG. 8E shows CFU-F assays for wild type BMSCs in the presence or absence of 1 μM DAPT. The arrow denotes a typical "type I" CFU-F.

FIG. 10 depicts high bone-mass in Prx1-Cre; RBP-Jκ$^{f/f}$ (PRBP) mice at 8 weeks. (A-B) X-ray radiography of the tibia. (C1-D1, C2-D2) 3-D μCT reconstruction of a 1.6-mm-long trabecular region immediately below the tibial growth plate, shown in lateral view (C1-D1) and top view (C2-D2). Threshold 200. Scale bar 1 mm.

DETAILED DESCRIPTION OF THE INVENTION

Figure 1E:
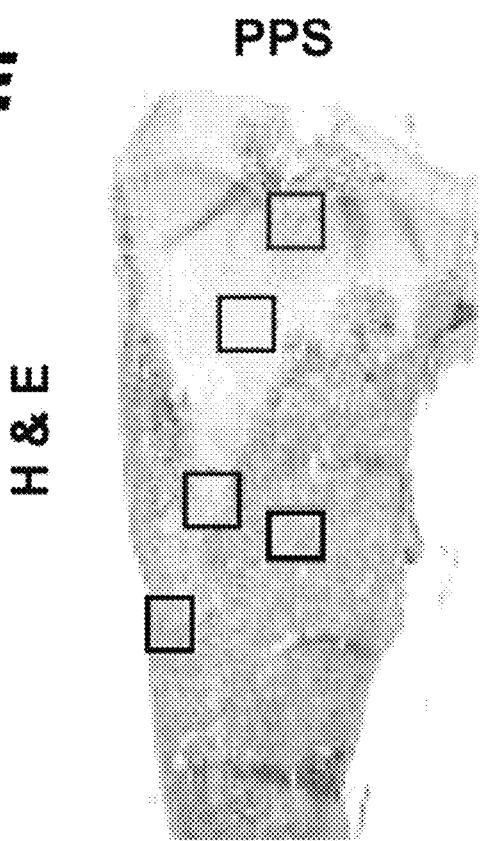
FIG. 1 demonstrates the skeletal phenotype of Prx1Cre, PS1$^{c/c}$, and PS2$^{n/n}$ mice (hereafter PPS mice) at 8 weeks of age. X-ray radiographs of hindlimbs are shown in FIGS. 1A and 1B. Red double-headed arrows denote the length of the tibia. Green arrowheads point to the trabecular bone region. Medial, longitudinal sections through 3-D reconstruction of the tibia by µCT are shown in FIGS. 1C and 1D. (Double-headed arrow: expanded growth plate; asterisk: excessive bone; arrow: normal growth plate). H&E staining of medial longitudinal sections through the tibia are shown in FIGS. 1E and 1K.
FIGS. 1F-1J show higher magnification of areas boxed in corresponding colors in FIG. 1E.
FIGS. 1L-1N show higher magnification of areas boxed in corresponding colors in FIG. 1K. (2°: secondary ossification center; NH: nonhypertrophic region; H: hypertrophic region; TB: trabecular bone; M: marrow).

It has been discovered, as illustrated in the examples, that modulating Notch signaling activity results in the modulation of bone resorption and deposition. In particular, it has been discovered that repression of the Notch signaling pathway by application of a gamma-secretase inhibitor, increases bone formation. The present invention, accordingly, includes compositions and methods for modulating bone resorption and bone deposition levels by modulating Notch signaling. The discoveries provide new treatment strategies for bone loss associated diseases and disorders. Exemplary bone loss associated disorders that may be treated by the method of the invention include, but are not limited to, osteoporosis, rickets, osteomalacia, McCune-Albright syndrome, and Paget's disease, as well as bone density loss promoted by the treatment of HIV/AIDs, autoimmune disease, epilepsy, juvenile rheumatoid arthritis, and the like.

I. Methods for Promoting Osteogenesis

One aspect of the present invention encompasses methods to treat, prevent, or delay bone loss in a subject. The methods may be utilized to treat a subject that is at risk of developing bone loss or to treat a subject that already has exhibited bone loss. In this context, an embodiment of the present invention includes a method for promoting osteogenesis in a subject by administering a Notch inhibitor. In some embodiments, the method may be in vitro. Alternatively, in other embodiments the method may be in vivo.

Methods of the invention may be used to identify or monitor particular subjects with, or at risk of, bone density defects. Subjects with, or at risk of, bone density defects, include but are not limited to the following: malnourished subjects; subjects living in poverty or malnutrition conditions; subjects that are elderly or chronically ill; subjects with bone disease such as those with osteoporosis, Paget's disease, bone metastasis, Rickets, osteogenesis imperfecta or other bone disease associated with altered bone density; subjects with autoimmune diseases, kidney disease, hyperparathyroidism, or Vitamin D deficiency; subjects being treated with treatments resulting in bone loss such as those for HIV/AIDs, autoimmune disease, epilepsy, juvenile rheumatoid arthritis, chronic glucocorticoid therapy and the like; and subjects undergoing bone repair or healing. A skilled artisan will recognize that the methods of the invention may appropriately be used to monitor or detect other diseases and disorders associated with or resulting from bone loss and defective osteogenesis.

Typically, the method of the invention may be utilized for any mammalian subject. Such mammalian subjects include, but are not limited to, human subjects or subjects and companion animals. Exemplary companion animals may include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value.

(a) Modulating Notch Signaling Activity

The requisite Notch signaling activity can be modulated by treating a subject with an effective amount of a Notch regulator. The Notch regulator may be an antagonist or agonist that results in decreased or increased Notch signaling activity, respectively. Suitable Notch regulators include, but are not limited to, antibodies, peptides, proteins, small molecules, or a combination thereof.

In exemplary embodiments, Notch signaling activity is decreased. In this context, the invention contemplates the use of Notch regulator peptides, proteins, antibodies, and small molecules derived from Notch and gamma-secretase pathways that resultantly inhibit Notch signaling. Notch regulators, such as antagonists and agonists, may alter Notch signaling activity either directly or indirectly. Such peptides may provide the basis of therapeutics by their inherent properties. Indirect modulation of Notch signaling can occur at any step of the NICD cleavage and release process including at the nucleic acid level, transcriptional level, translational level, protein-folding level, or enzymatic cleavage level. Suitable Notch signaling antagonists are typically capable of preventing or reducing Notch signaling, while Notch signaling agonists typically induce or increase Notch signaling activity. Methods known in the art may be used to design and generate Notch regulator peptides, proteins, antibodies, and small molecules.

In an exemplary embodiment, the Notch inhibitor is a gamma-secretase inhibitor. The gamma-secretase pathway inhibitor may comprise an inhibitor selected from the group consisting of a dipeptide class gamma-secretase pathway inhibitor, a sulfonamide class gamma-secretase inhibitor, a transition state mimic class gamma-secretase inhibitor, a benzocaprolactam class gamma-secretase inhibitor, and gamma-secretase inhibitors known in the art. By way of example, the gamma-secretase pathway inhibitor may be selected from the group consisting of DAPT (N—[N-(3,5-Difluorophenacetyl-L-alanyl)]-S-phenylglycine t-Butyl Ester), 1-(S)-endo-N-(1, 3,3)-Trimethylbicyclo[2.2.1]hept-2-yl)-4-fluorophenyl Sulfonamide, WPE-III31C, S-3-[N'-(3,5-difluorophenyl-alpha-hydroxyacetyl)-L-alanilyl]amino-2,3-dihydro-1-methyl-5-phenyl-1H-1,4-benzodiazepin-2-one, and (N)-[(S)-2-hydroxy-3-methyl-butyryl]-1-(L-alaninyl)-(S)-1-amino-3-methyl-4,5,6,7-tetrahydro-2H-3-benzazepin-2-one.

Additional inhibitors of the gamma-secretase pathway can be identified. For example, medicinal and combinatorial chemistry methods well known to those skilled in the art can be used to modify known PS-1 antagonists to form new gamma-secretase inhibitors with improved efficacy for the purposes of the present invention. Further, analogs of the above-named compounds may be used. Known gamma-secretase inhibitors rely on the known role of the gamma-secretase pathway, making some inhibitors more and some inhibitors less effective at influencing bone growth. Accordingly, known factors may also be evaluated for their ability to create the results desired for the novel application disclosed herein.

In certain embodiments, the Notch inhibitor may be a RBP-Jκ inhibitor. RBP-Jκ is a transcription factor that recognizes the sequence C(T)GTGGGA. Inhibitors of RBP-Jκ may be identified. For example, medicinal and combinatorial chemistry methods well known to those skilled in the art can be used to modify known RBP-Jκ antagonists to form new RBP-Jκ inhibitors with improved efficacy for the purposes of the present invention. Further, analogs of the above-identified compounds may be used.

(b) In Vivo Induction of Osteogenesis

Notch regulators may be used to induce osteogenesis in vivo. In this context, the Notch regulators may be administered to an individual, e.g., a mammal such as a human, in an amount effective to induce differentiation of mammalian cells into cells of an osteoblast lineage. In view of their ability to induce osteogenesis, the Notch regulators are useful for treating bone disorders and diseases. In a preferred embodiment, Notch regulators may be used to treat osteoporosis. In a preferred embodiment, Notch regulators may be used to increase bone density. In a particularly preferred embodiment, Notch regulators may be used to increase bone density and reduce bone loss.

One of skill in the art will appreciate that the Notch regulators may be used alone or in combination with other compounds and therapeutic regimens to induce osteogenesis. For example, a notch regulator may be administered in conjunction with other factors that are involved in the bone remodeling cycle, including bone morphogenetic proteins or anti-resorbtive medications. Suitable bone morphogenetic proteins include, for example, BMP-2, BMP-4, and BMP-7. Suitable anti-resorbtive medications include, for example, bisphosphonates such as, for example, alendronate sodium and risedronate sodium; hormones, such as, for example, calcitonin and estrogens, and selective estrogen receptor modulators, such as, for example, raloxifene.

Formulations suitable for oral administration may consist of (a) liquid solutions, such as an effective amount of the Notch regulator suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms may include one or more of the following: lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms may comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Notch regulators may be in formulations suitable for other routes of administration, such as, for example, intravenous infusion, intraperitoneally, or subcutaneously. The formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. Injection solutions and suspensions can be prepared from sterile powders, granules, and tablets.

The amount of Notch regulator administered to a subject typically can and will vary. In general, the amount is typically sufficient to affect a beneficial therapeutic response in the subject over time compared to no treatment at all. For example, if the Notch regulators are administered to treat or prevent osteoporosis, the amount administered to the subject is generally sufficient to substantially prevent, retard, or reverse decreases in bone density. The amount is typically determined by the efficacy of the particular composition employed and the condition of the subject, as well as the body weight or surface area of the subject to be treated.

(c) In Vitro Induction of Osteogenesis

The Notch regulators may conveniently be used to induce osteogenesis in vitro. In this iteration of the invention, mammalian cells are contacted with the Notch regulators, whereupon the mammalian cells differentiate into cells of an osteoblast lineage.

The mammalian cells can be stem cells, typically mesenchymal stem cells (MSCs), pre-osteoblasts, or cells of other lineages such as, for example, pre-adipocytes or myoblasts. Methods for isolation and differentiation of human and animal MSCs have been described (see, e.g., U.S. Pat. Nos. 5,942,225 and 5,486,359; and Pittenger et al., Science 284: 143 (1999)).

Human mesenchymal stem cells (MSC) may be obtained by isolating pluripotent mesenchymal stem cells from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, blood, adipose tissue, and muscle satellite cells. Typically, cells from a tissue specimen containing mesenchymal stem cells are cultured in growth medium containing growth factors that (1) stimulate mesenchymal stem cell growth without differentiation, and (2) allow for the selective adherence of only the mesenchymal stem cells to a substrate surface. After culturing the cells for a suitable amount of time, non-adherent matter is removed from the substrate surface, thus providing an expanded population of mesenchymal stem cells. Thus, homogeneous MSC populations are obtained by positive selection of adherent marrow or periosteal cells that are free of markers associated with either hematopoietic cells or differentiated mesenchymal cells.

The cells to be differentiated into cells of an osteoblast lineage can be derived from any suitable mammal. For example, the cells may be obtained from a rodents such as, for example, mice, rats, guinea pigs, and rabbits; non-rodent mammals such as, for example, dogs, cats, pigs, sheep, horses, cows, and goats; primates such as, for example, chimpanzees and humans. The cells to be differentiated may be primary cells or may be cells maintained in culture. If the cells are maintained in culture, they are typically contacted with the compounds/compositions of the present invention between the 12th and 15th passage in culture. Techniques and methods for establishing a primary culture of cells for use in the methods of the invention are known to those of skill in the art (see, e.g., Humason, *Animal Tissue Techniques*, 4th ed., W. H. Freeman and Company (1979), and Ricciardelli et al., (1989) In Vitro Cell Dev. Biol. 25: 1016).

(d) Administration of Differentiated Osteoblast Cells

Differentiated osteoblast cells produced by the in vitro method detailed herein may be administered to a subject for treatment a variety of indications, such as bone loss associated diseases and disorders. In one embodiment of the invention, differentiated osteoblast cells on an intact solid support (e.g., a three-dimensional matrix or a planar surface) can be administered to the subject, e.g., via surgical implantation. Alternatively, the differentiated osteoblast cells can be detached from the matrix, i.e., by treatment with a protease, before administration to the subject, e.g., intravenous, subcutaneous, or intraperitoneal.

In some embodiments of the present invention, mesenchymal stem cells are extracted from a human and subsequently contacted with a matrix for proliferation and differentiation into cells of an osteoblastic cell lineage. Cells can be extracted from the subject to be treated, i.e., autologous (thereby avoiding immune-based rejection of the implant), or can be from a second subject, i.e., heterologous. In either case, administration of cells can be combined with an appropriate immunosuppressive treatment.

Osteoblast cells differentiated according to the methods of the present invention may be administered to a subject by any means known in the art. Suitable means of administration include, for example, intravenous, subcutaneous, intraperitoneal, and surgical implantation.

For surgical implantation, differentiated cells are typically left on an intact solid support, e.g., a three-dimensional matrix or planar surface. The matrix or planar surface is surgically implanted into the appropriate site in a subject. For example, a subject needing a bone graft can have differentiated cells on an intact solid support surgically implanted.

In determining the effective amount of the cells to be administered in the treatment or prophylaxis of conditions owing to diminished or aberrant osteoblasts, the physician evaluates cell toxicity, transplantation reactions, progression of the disease, and the production of anti-cell antibodies. For administration, osteoblast cells differentiated according to the methods of the present invention can be administered in an amount effective to provide osteoblasts to the subject, taking into account the side-effects of the osteoblasts at various concentrations, as applied to the mass and overall health of the subject. Administration may be accomplished via single or multiple doses.

(e) Detection of Osteogenesis

After administration of the Notch regulators either in vivo or in vitro, induction of osteogenesis may be detected by several suitable means. In one embodiment, osteogenesis may be detected by measuring expression of osteoblast-specific proteins, detecting expression of bone-specific transcription factors, and detecting changes in bone density. Osteoblast-specific proteins include, for example, alkaline phosphatase (ALP), collagen type I, osteocalcin, and osteoponin (see, e.g., Olsen et al., Annu. Rev. Cell. Dev. Biol. 16:191 (2000)). Typically, expression of alkaline phosphatase is detected as an indicator of osteogenesis. Bone specific transcription factors include, for example, Cbfa1/Runx2, gsc, Dlx1, Dlx5, Msx1, Cart1, Hoxa1, Hoxa2, Hoxa3, Hoxbl, rae28, Twist, AP-2, Mf1, Pax1, Pax3, Pax9, TBX3, TBX4, TBX5, and Brachyury (see, e.g., Olsen et al, 2000 supra). Typically, expression of Cbfa1/Runx2 is detected as an indicator of osteogenesis.

Expression of osteoblast-specific proteins may be detected by measuring the level of the osteoblast-specific protein or mRNA. The level of particular osteoblast-specific proteins can conveniently be measured using immunoassays such as immunohistochemical staining, western blotting, ELISA and the like with an antibody that selectively binds to the particular osteoblast specific proteins or a fragment thereof. Detection of the protein using protein-specific antibodies in immunoassays is known to those of skill in the art (see, e.g., Harlow & Lane, Antibodies: A Laboratory Manual (1988), Coligan, Current Protocols in Immunology (1991); Goding, Monoclonal Antibodies: Principles and Practice (2d ed. 1986); and Kohler & Milstein, Nature 256:495-497 (1975). For measurement of mRNA, amplification, e.g., PCR, LCR, or hybridization assays, e.g., northern hybridization, RNAse protection, dot blotting, are preferred. The level of protein or mRNA is detected, for example, using directly or indirectly labeled detection agents, e.g., fluorescently or radioactively labeled nucleic acids, radioactively or enzymatically labeled antibodies. These assays are well known to those of skill in the art and described in, e.g., Ausubel, et al. ed. *Current Protocols In Molecular Biology* (2001).

Typically, expression of the osteoblast specific-protein, alkaline phosphatase, is used to detect differentiated osteoblasts. Expression of alkaline phosphatase (ALP) is correlated with osteogenesis. ALP hydrolyzes inorganic pyrophosphates to phosphates and promotes the formation of hydroxyapatite crystals in bone matrix. Deactivating mutations of ALP cause osteomalacia, characterized by poorly mineralized bones and frequent bone fractures, indicating that ALP plays a significant role in bone formation (see, e.g., Hessle et al., Proc. Natl. Acad. Sci. USA. 99:9445 (2002)). ALP is a highly active and stable enzyme, making direct assays of its enzymatic activity convenient. In addition, direct histochemical staining of cells can conveniently be used to detect ALP.

For direct assays of ALP activity, cells are plated in 384-well plates and treated with an appropriate amount of a Notch regulator, either alone or with other growth factors (e.g., BMP-4) and then incubated at 37° C. in 5% $CO_2$. After an appropriate incubation time, the media is removed and lysis buffer is added into each well. After an appropriate incubation time in lysis buffer, alkaline phosphatase substrate solution (e.g., 2'-[2'-benzothiazoyl]-6'-hydroxybenzothiazole phosphate (BBTP)) is added to each well. After an appropriate incubation time at room temperature, the plates are read on a plate reader using methods known in the art.

For direct immunohistochemical staining of cells to detect ALP, cells are seeded in 96-well assay plates at a suitable density and treated with an appropriate amount of a Notch regulator, either alone or with other growth factors (e.g., BMP-4) for an appropriate time. Cells are then and fixed in a 10% formalin solution. The fixed cells are washed again and stained with a reagent specific for ALP (e.g., an antibody specific for ALP or a colorimetric ALP substrate) using methods known to those of skill in the art (see, e.g., Harlow & Lane, 1988, supra; Coligan, 1991, supra; Goding, 1986, supra; and Kohler & Milstein, 1975, supra). Photographic images of the cells are taken and ALP positive cells are counted manually from the images.

Expression of bone-specific transcription factors can be detected using reporter gene assays. These assays are well known to those of skill in the art and are described in, e.g., Ausebel et al., supra. Expression of the bone specific transcription factor Cbfa1/Runx2 is typically used to detect osteogenesis. Cbfa1/Runx2 plays an essential role in osteoblast differentiation transgenic mice lacking the Cbfa1/Runx2 gene die shortly after birth due to loss in bone formation (see, e.g., Ducy et al., Cell 89:747 (1997) and Komori et al., Cell 89:755 (1997)).

Reporter genes such as, for example, chloramphenicol acetyltransferase, firefly luciferase, bacterial luciferase, or beta-galactosidase can be used in the reporter gene assays. The reporter construct is typically transiently or stably transfected into a cell. The promoter region of the relevant gene is typically amplified by PCR appropriate primers. The resulting PCR product is inserted into a suitable cloning vector, amplified and sequenced. The resulting plasmid is digested with appropriate restriction enzymes and the resulting fragment is inserted into a vector comprising a reporter gene.

For reporter gene assays with transiently transfected cells, the cells are typically seeded in a 6-well plate at a density of 30,000 cells/well in 2 mL of growth medium and incubated overnight or for a suitable time. Plasmid DNA is transfected into the cells using a suitable transfection reagent. After 8 hours, the transfected cells are plated into 96-well assay plates (e.g., Corning) and treated with an appropriate amount of a Notch regulator. The cells are incubated for 4 days, and then the reporter gene activity in the cells is assayed using methods known to those of skill in the art.

For reporter gene assays with stably transfected cells, the cells are typically seeded in a 6-well plate at a density of 30,000 cells/well in 2 mL of growth medium and incubated overnight or for a suitable time. An appropriate amount of reporter plasmid and a vector comprising a selectable marker (e.g., an antibiotic resistance gene) are co-transfected into the cells using an appropriate transfection reagent. After an appropriate incubation time, cells are seeded in a 10 cm culture dish and an appropriate amount of antibiotic is added to the culture medium. Fresh antibiotic is added at appropriate intervals. The antibiotic resistant colonies are pooled to yield the stably transfected cells. The transfected cells are plated into 96-well assay plates (e.g., Corning) and treated with an appropriate amount of a Notch regulator. The cells are incubated for 4 days, then the reporter gene activity in the cells is assayed using methods known to those of skill in the art.

To assess the effect of Notch regulators on bone density, a baseline measurement of bone density in an individual who will receive treatment may have been taken. Bone density is periodically measured at suitable intervals during and after administration of the Notch regulator. Methods and devices for measuring bone density are well known in the art and are described in, e.g., U.S. Pat. Nos. 6,436,042; 6,405,068; 6,320,931; 6,302,582; 6,246,745; 6,230,036; 6,213,934; 6,102,567; 6,058,157; 5,898,753; 5,891,033; 5,852,647; 5,817,020; 5,782,763; 5,778,045; 5,749,363; 5,745,544; 5,715,820; 5,712,892; 5,572,998; and 5,480,439.

Methods are available for monitoring the gamma-secretase pathway, which can facilitate, inter alia, analysis of the efficacy of gamma-secretase based Notch regulators. For example, monitoring activity of the gamma-secretase pathway could be accomplished by creating a substrate for the gamma-secretase that can be detected in various assays. For instance, Kinoshita et al. (2002, J. Neurochem. 82:839-47) describes that the gamma secretase-generated carboxyl-terminal domain of APP (APP-CT) interacts in the cytoplasm with an adapter protein, Fe65, and this CT domain, when tagged with green fluorescent protein (GFP), may serve as a readout for processes that modify gamma secretase release of the APP-CT. The release can be monitored by colocalization microscopy, fluorescence resonance energy transfer (FRET), bioluminescence resonance energy transfer (BRET), ELISA assays detecting processed APP fragments, and other methods known in the art. Other methods of detecting gamma-secretase inhibitor activity include those described in U.S. Patent Application No. 2006/0264380 and in the art.

II. Kits

In another aspect, the invention provides articles of manufacture and kits containing materials useful for treating the pathological conditions described herein. The article of manufacture may include a container of a medicament as described herein with a label. Suitable containers include, for example, bottles, vials, and test tubes. The containers may be formed from a variety of materials such as glass or plastic. The container holds a composition having an active agent that is effective for treating, for example, diseases characterized by bone loss. The active agent in the composition is a Notch regulator of the invention, including a peptide, protein, antibody, small molecule, or an agent such as a vector or cell preparation capable of allowing production of a Notch regulator agent in vivo. The label on the container may indicate that the composition is used for treating bone disorders, and may also indicate directions for administration and monitoring techniques, such as those described above.

A kit of the invention includes the container described above and a second container, which may include a pharmaceutically acceptable diluent as is commonly known in the art. It may further include other materials desirable from a commercial and user standpoint, including other buffers, diluents, filters, needles, syringes, and package inserts with instructions for use.

DEFINITIONS

"Osteogenesis," as used herein, refers to proliferation of bone cells and growth of bone tissue (i.e., synthesis and deposit of new bone matrix). Osteogenesis also refers to differentiation or transdifferentiation of progenitor or precursor cells into bone cells (i.e., osteoblasts). Progenitor or precursor cells can be pluripotent stem cells such as, e.g., mesenchymal stem cells. Progenitor or precursor cells can be cells pre-committed to an osteoblast lineage (e.g., pre-osteoblast cells) or cells that are not pre-committed to an osteoblast lineage (e.g., pre-adipocytes or myoblasts).

A "stem cell," as used herein, refers to any self-renewing pluripotent cell, multipotent cell, progenitor cell, or precursor cell that is capable of differentiating into multiple cell types. Stem cells suitable for use in the methods of the present invention include those that are capable of differentiating into cells of osteoblast lineage, e.g., osteoblasts. Suitable stem cells for use in the methods of the present invention include, for example, mesenchymal stem cells, pre-osteoblast cells, pre-adipocyte cells, and myoblast cells. Mesenchymal stem cells (MSC) are capable of differentiating into the mesenchymal cell lineages, such as bone, cartilage, adipose, muscle, stroma, including hematopoietic supportive stroma, and tendon, and play important roles in repair and regeneration. MSCs are identified by specific cell surface markers that are identified with unique monoclonal antibodies as described in U.S. Pat. No. 5,643,736.

"Differentiate" or "differentiation," as used herein, refers to the process by which precursor or progenitor cells (i.e., stem cells) differentiate into specific cell types, e.g., osteoblasts. Differentiated cells can be identified by their patterns of gene expression and cell surface protein expression. Typically, cells of an osteoblast lineage express genes such as, for example, alkaline phosphatase, collagen type I, osteocalcin, and osteoponin. Typically, cells of an osteoblast lineage express bone specific transcription factors such as, for example, Cbfa1/Runx2 and Osx (see, Nakashima et al., Cell 108(1):17-29 (2002)). Additional transcription factors that are involved in osteoblast differentiation include, e.g., gsc, Dlx1, Dlx5, Msx1, Cart1, Hoxa1, Hoxa2, Hoxa3, Hoxbl, rae28, Twist, AP-2, Mf1, Pax1, Pax3, Pax9, TBX3, TBX4, TBX5, and Brachyury.

"Transdifferentiation" refers to the process by which precursor or progenitor cells (i.e., stem cells) pre-committed to cell types of one lineage differentiate into specific cell types of another lineage, e.g., pre-adipocytes transdifferentiate into osteoblasts or myoblasts transdifferentiate into osteoblasts. Transdifferentiated cells can be identified by their patterns of gene expression and cell surface protein expression. Typically, cells of an osteoblast lineage express genes such as, for example, alkaline phosphatase, collagen type I, osteocalcin, and osteoponin. Typically, cells of an osteoblast lineage express bone specific transcription factors such as, for example, Cbfa1/Runx2 and Osx (see, Nakashima et al., Cell 108(1):17-29 (2002). Additional transcription factors that are involved in osteoblast differentiation include, e.g., gsc, Dlx1, Dlx5, Msx1, Cart1, Hoxa1, Hoxa2, Hoxa3, Hoxbl, rae28, Twist, AP-2, Mf1, Pax1, Pax3, Pax9, TBX3, TBX4, TBX5, and Brachyury.

"Culturing," as used herein, refers to maintaining cells under conditions in which they can proliferate, differentiate, and avoid senescence. For example, in the present invention, cultured mesenchymal stem cells proliferate and differentiate into cells of an osteoblastic cell lineage. Cells can be cultured in growth media containing appropriate growth factors, i.e., a growth factor cocktail that contains, for example, bone morphogenetic protein-2 (BMP-2), bone morphogenetic protein-4 (BMP-4), bone morphogenetic protein-7 (BMP-7), or another suitable member of the BMP family of proteins.

As used herein "gamma-secretase inhibitor" means any material or compound that, e.g., binds to, partially or totally blocks activity, decreases, prevents, delays activation, inactivates, desensitizes, or down regulates the activity or expression of gamma-secretase or the gamma-secretase pathway. Inhibitors include genetically modified versions of gamma-secretase proteins, e.g., versions with altered activity, as well as naturally occurring and synthetic ligands, antagonists, agonists, antibodies, small chemical molecules and the like. "Inhibitor", as the term is used herein, includes but is not limited to an antagonist.

The phrase "pharmaceutically effective amount" is used herein to mean an amount sufficient to initiate or increase to some beneficial degree, preferably to increase by at least about 8, 9, 10, 12, 15, 20, or 25 percent, more preferably by at least about 30, 35, 40, 45, 50, 60, 70, 80, or 90 percent, and more preferably by at least 91 percent or higher, bone growth as compared to untreated controls.

The phrase "pharmaceutically acceptable" refers to molecular entities and compositions that are physiologically tolerable and do not typically produce an allergic or similar untoward reaction when administered to a subject.

An "effective amount" is a pharmaceutically-effective amount that is intended to qualify the amount of an agent or compound, that when administered to a subject, will achieve the goal of preventing, delaying, or treating bone density loss associated bone loss disease, disorders, and effects of some treatments.

The terms "modulate," "modulating," and "altering," as used herein, are used in their broadest interpretation and refer to a change in the biological activity of a biologically active molecule. Modulation, or altering, may be an increase or a decrease in activity, a change in binding characteristics, or any other change in the biological, functional, or immunological properties of biologically active molecules.

The term "treat" or "treatment" as used herein in the context of bone loss associated disorders, includes preventing bone density loss before it occurs, reducing loss after it occurs, or restoring lost bone density.

As various changes could be made in the above compositions and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Methods Used in Examples 1-6

Analyses of mice. Radiographs of mouse hind limbs were generated using a Faxitron X-ray system (Faxitron X-ray Corp). Micro computed tomography (µCT 40, Scanco Medical AG) was used for three-dimensional reconstruction. Histology was performed on paraffin sections, following decalcification for postnatal samples. For dynamic histomorphometry of postnatal mice, calcein (Sigma) was injected intraparitoneally at 7.5 mg/kg on days 7 and 2 prior to sacrifice, and tibias were sectioned in methyl-methacrylate. In situ hybridization and BrdU labeling were performed as described in the art. Quantitation of bone parameters was performed using the Osteomeasure Analysis System (Osteometrics). CTX-I assays were done using RatLaps ELISA (Nordic Bioscience Diagnostics).

Cell cultures. Bone marrow harvests and high-density cultures were done as described in the art. For CFU-F assays, single-cell suspension of nucleated bone marrow cells were seeded at $3 \times 10^6$ on T25 flasks and cultured in DMEM (Invitrogen) containing 20% lot-selected FBS (Hyclone) and 1-Thioglycerol (Sigma) for 11-14 days without change of medium. For CFU-F assays, colonies with more than 50 small, round or spindle-shaped cells in direct contact with each other were scored as "type I" CFU-Fs. Clusters with more than 100 cells including large cells with multiple processes were counted as "type II" CFU-Fs. Differentiation of BMSCs was induced by either osteogenic (50 µg/ml ascorbic acid, 50 mM β-glycerol-2-phosphate) or adipogenic (0.5 µMIBMX, 60 µM indomethacine, 0.5 µM hydrocortisone) DMEM containing 10% FBS (Atlas). Primary osteoblasts were isolated from long bones by incubating cleaned small bone chips to allow cells to migrate onto culture dishes. NICD was detected by Western analyses using a specific antibody (Cell Signaling).

Example 2

Removal of γ-Secretase in Early Mesenchyme Specifically Affects the Endochondral Skeleton PS1 and PS2 gene expression was removed using Prx1Cre mice to abolish all Notch signaling selectively from the early mesenchyme of the calvaria and the limb primordium. Mice of the genotype Prx1Cre; PS1$^{c/c}$; PS2$^{n/n}$ (hereafter PPS mutants, c: floxed allele, n: null allele) were born at the Mendelian ratio and appeared normal except for variable digit anomalies, but all died between 9 and 10 weeks of age from unknown causes.

Figure 1F:
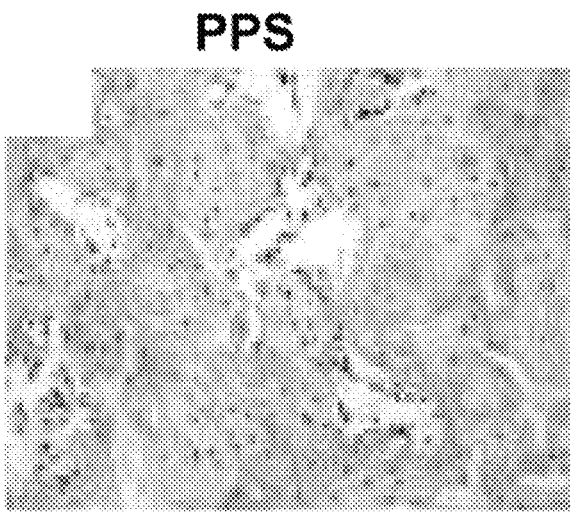
Figure 1G:
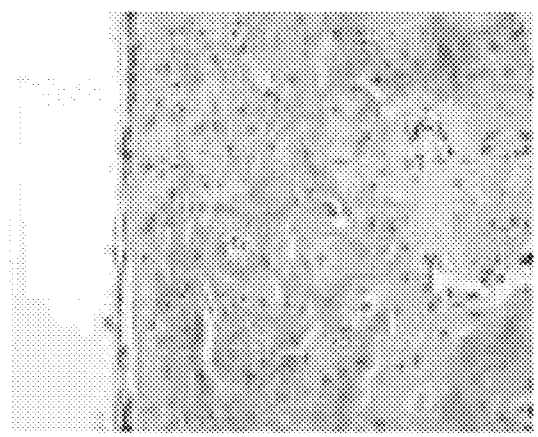
Figure 1H:
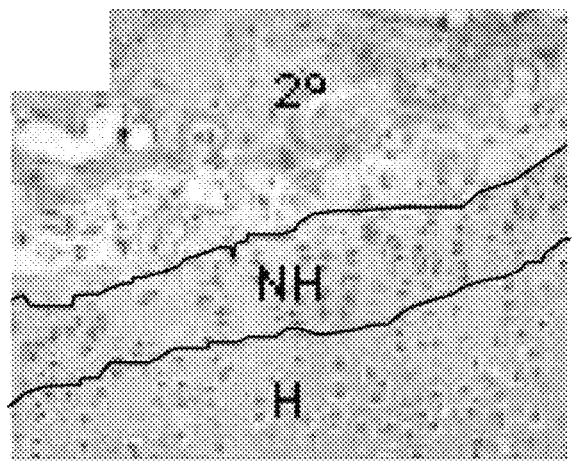
Figure 1I:
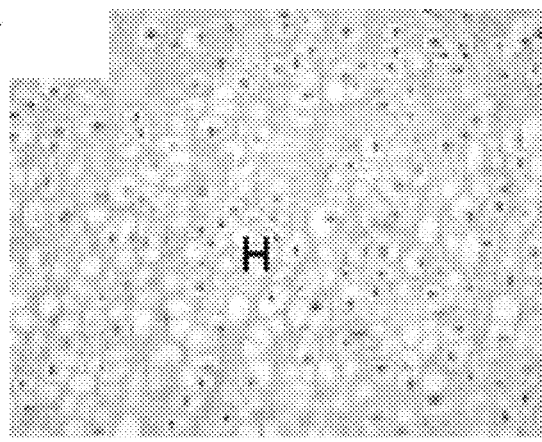
Figure 1J:
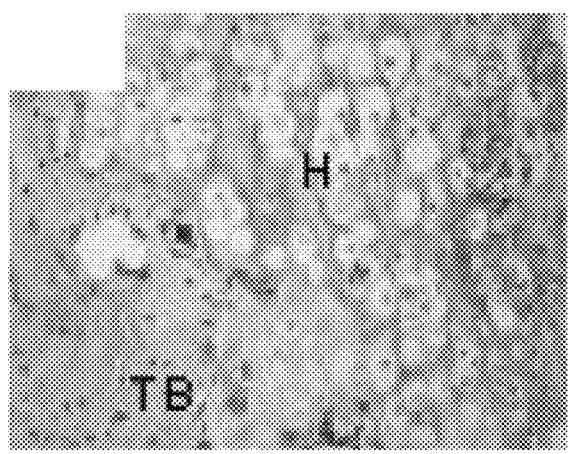
Figure 1K:
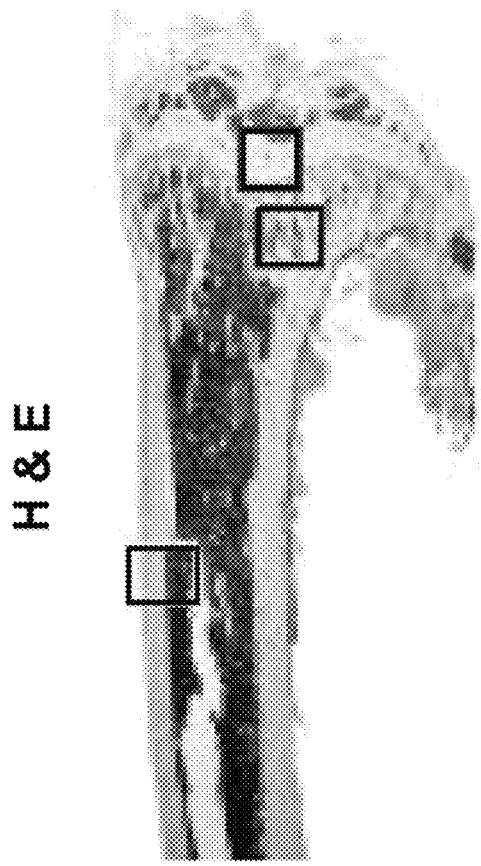
Figure 1L:
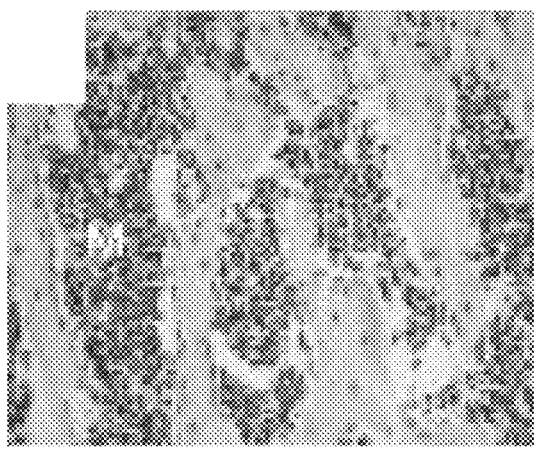
Figure 1M:
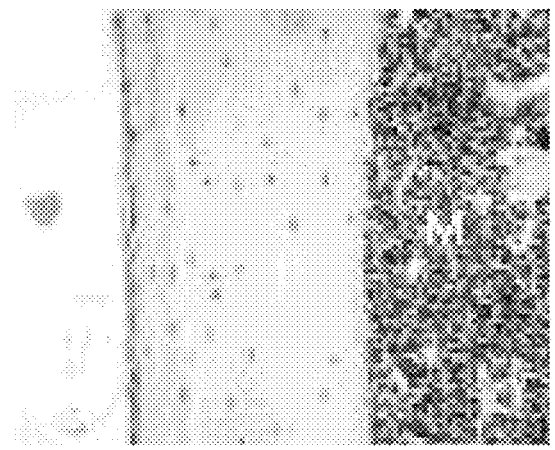
Figure 1N:
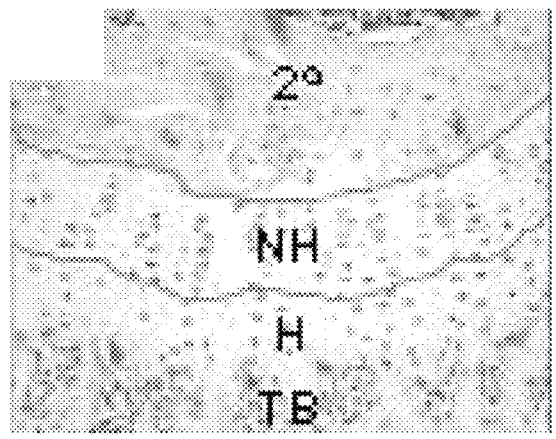
Figures 2A, 2B, 2C, 2D:
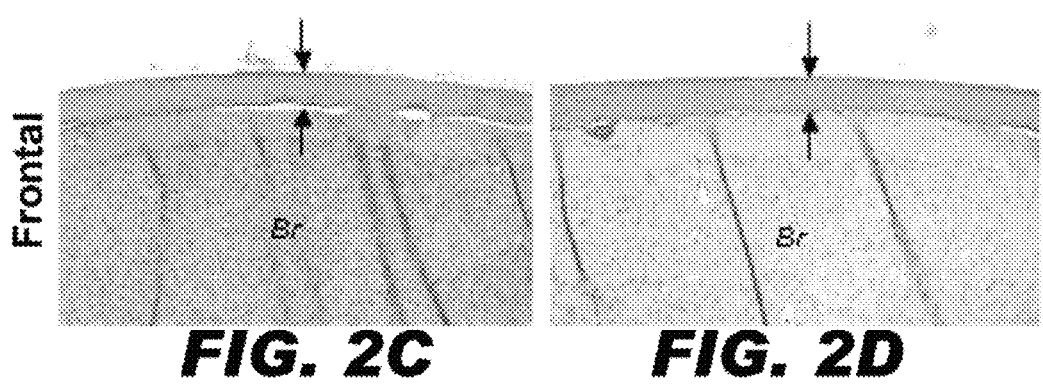
FIG. 2 shows H&E staining of sections through the parietal (FIGS. 2A and 2B) and the frontal bone (FIGS. 2C and 2D) of PPS versus control littermates at 8 weeks of age. (M: marrow; Br: brain; arrows mark calvarial thickness).

Morphological analyses of the skeleton revealed a dramatic phenotype in postnatal mutant mice at 8 weeks of age. X-ray radiography indicated that PPS mutant mice not only had shorter long bones in the limbs when compared with littermate controls (PS2$^{n/n}$, no obvious phenotype), but also exhibited a marked increase in radio density within the bone marrow cavity (FIGS. 1A and 1B). Three-D reconstruction of the tibia using micro computed-tomography (µCT) confirmed that a massive accumulation of bone (asterisk) occluded much of the presumptive marrow cavity in the mutant (FIG. 1C). In addition, the radiolucent growth plate cartilage was greatly elongated in the mutant (FIGS. 1C and 1D). Histology of longitudinal sections through the medial portion of the tibia further demonstrated that PPS mutants contained excessive cancellous bone encapsulating a dramatic "wedge shaped" extension of the growth plate cartilage (FIGS. 1E and 1F). Examination at a higher magnification indicated that the cartilage extension was chiefly due to accumulation of hypertrophic chondrocytes (FIG. 1H-1J), whereas the length of the nonhypertrophic region appeared unaltered (FIGS. 1H and 1N). In the most severe case, the mutant diaphysis appeared to be entirely filled with cancellous bone, with no recognizable marrow cavity or clear demarcation of cortical bone (FIG. 1G). Similarly, the secondary ossification center of the PPS mutant also contained excessive bone and no obvious marrow (FIG. 1H). Interestingly, the calvarium, also targeted by Prx1Cre, was not affected in the PPS mutant, a result confirmed by both X-ray radiography (data not shown) and histology (FIG. 2). Thus, removal of PS1 and PS2 resulted in the expansion of the hypertrophic cartilage and an excess of trabecular bone specifically in endochondral bones of postnatal animals.

Example 3

Deletion of Notch1 and Notch2 Resembles Removal of γ-Secretase

Figure 3E:
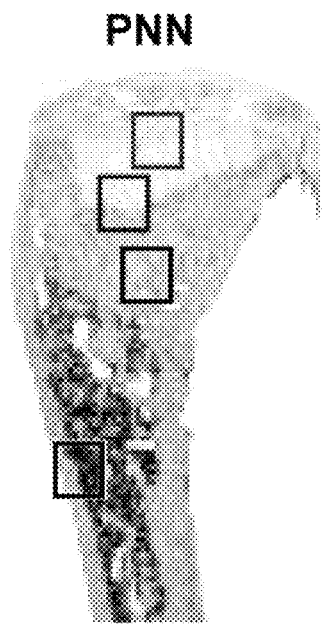
FIG. 3 demonstrates the skeletal phenotype of Prx1Cre; N1$^{n/c}$; and N2$^{c/c}$ (hereinafter PNN mutants) mice at 8 weeks of age. X-ray radiographs of hindlimbs are shown in FIGS. 3A and 3B. Red double-headed arrows denote the length of the tibia. Green arrowheads point to the trabecular bone region. Medial longitudinal sections through 3-D reconstruction of the tibia by µCT are shown in FIGS. 3C and 3D. (Double-headed arrow: expanded growth plate; asterisk: excessive bone; arrow: normal growth plate). H&E staining of medial longitudinal sections through the tibia are shown in FIGS. 3E and 3J.
FIGS. 3F-3I show higher magnification of areas boxed in corresponding colors in FIG. 3E.
FIG. 3K-3M show higher magnification of areas boxed in corresponding colors in FIG. 3J. (Abbreviations: 2°: secondary ossification center; NH: nonhypertrophic region; H: hypertrophic region; TB: trabecular bone; M: marrow).
FIGS. 3N and 3P show TRAP staining on medial longitudinal sections through the tibia. Osteoclasts stain red.
FIGS. 3O and 3Q show higher magnification of boxed areas in FIGS. 3N and 3P.
FIGS. 3R-3W depict area micrographs from longitudinal sections of tibias after calcein double labeling. The percentage of calcein double-labeled bone surface (Dls) over total bone surface (Tbs) in trabecular bone region is graphically illustrated in FIG. 3X ($p<0.05$, $n=3$). The number of osteoclasts (#OC) normalized to trabecular bone perimeter (mm) are graphically illustrated in FIG. 3Y ($p<0.05$, $n=3$).
FIG. 3Z shows assays for CTX-I in serum samples to measure in vivo osteoclast activity ($n=4$).
Figure 3F:
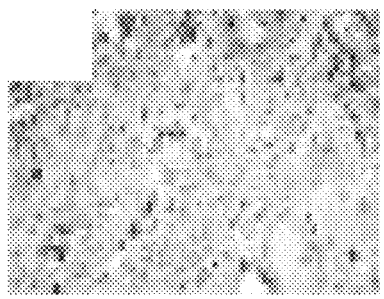
Figure 3G:
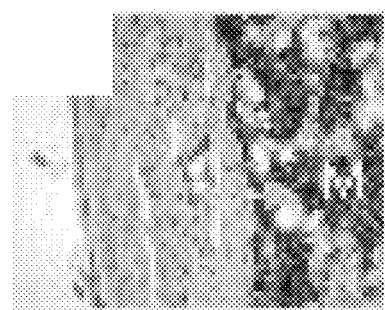
Figure 3H:
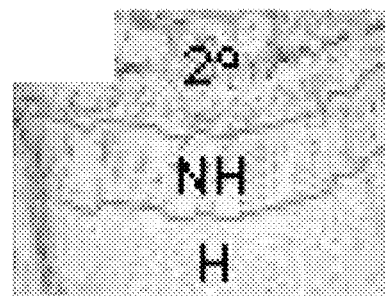
Figure 3I:
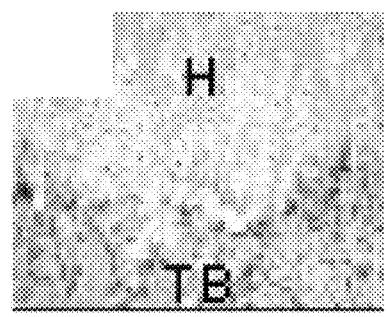
Figure 3J:
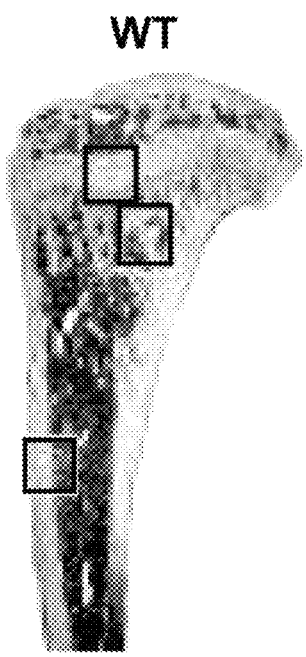
Figure 3K:
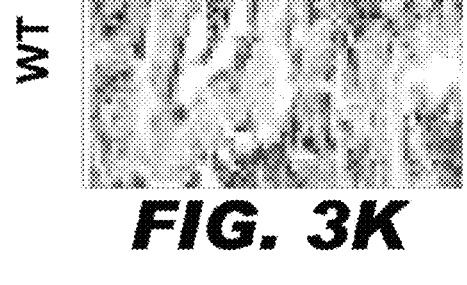
Figure 3L:
Figure 3M:
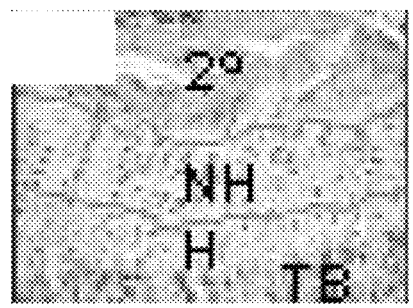
Figure 3N:
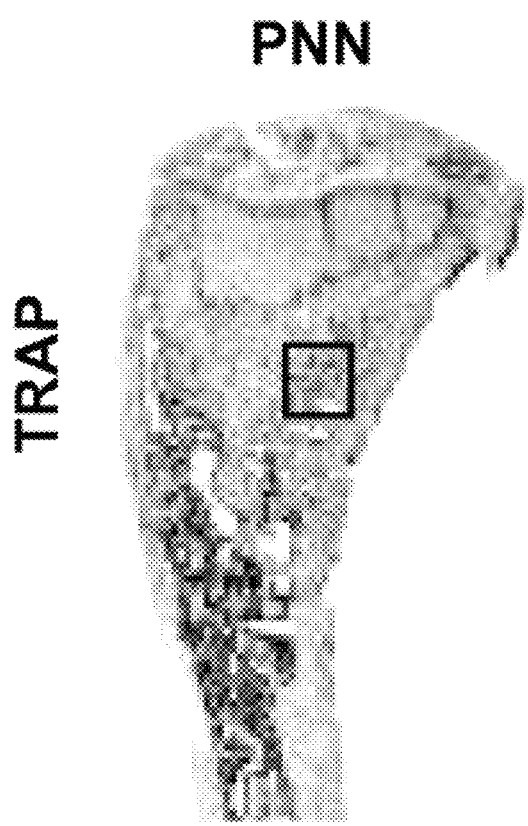
Figure 3O:
Figure 3P:
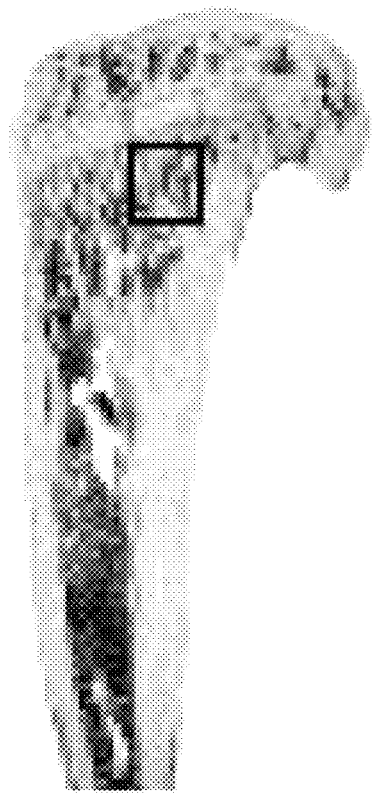
Figure 3Q:

The skeletal phenotype caused by the removal of γ-secretase prompted an investigation into whether abrogation of Notch signaling was specifically responsible. To this end, the same strategy to remove Notch1 (N1) and Notch2 (N2) from the early limb mesenchyme was used. Mice of the genotype Ptx1Cre; N1$^{n/c}$; N2$^{c/c}$ (hereafter PNN mutants) were born at the Mendelian ratio and lived with no apparent deficiency, but exhibited a skeletal phenotype remarkably similar to that of PPS mutants. In particular, X-ray radiography revealed that at 8 weeks of age the PNN mutants had notably shorter long bones, and markedly higher radio density within the trabecular bone region, when compared to wild type (N1$^{c/c}$; N2$^{c/c}$) littermates (FIGS. 3A and 3B). µCT analyses of the tibia confirmed both elongation of the radiolucent growth plate cartilage, and increase of bone mass within the marrow cavity of PNN mutants (FIGS. 3C and 3D). Finally, histology of the tibia revealed excessive trabecular bone encasing a "wedge-shaped" extension of the growth plate cartilage, and a notable reduction of the marrow space in both primary and secondary ossification centers of PNN mutants (FIGS. 3E and 3J). As seen in PPS mice, cartilage elongation in PNN animals was due to expansion of the hypertrophic zone (FIG. 3I), with no apparent increase in the nonhypertrophic region (FIGS. 3H and 3M). Interestingly, the increase in bone mass appeared to be limited to the trabecular region (FIGS. 3F and 3K); although the organization of the cortical bone appeared to be altered, no significant changes in cortical thickness were observed between mutant and wild type littermates (FIGS. 3G and 3L). Overall, PNN mutants exhibit a postnatal skeletal phenotype qualitatively identical to that of PPS mutants.

Figure 3X:
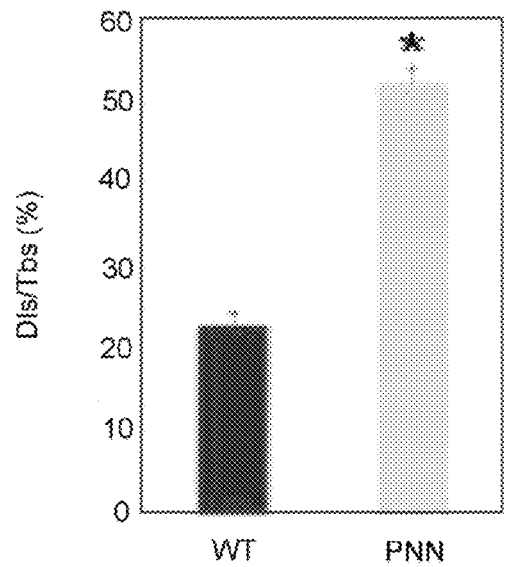
Figure 3Y:
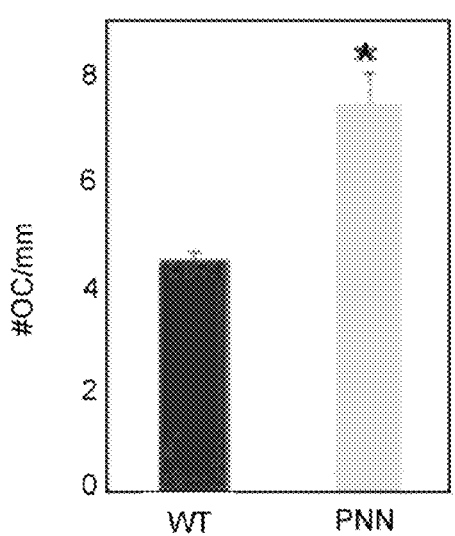
Figure 3Z:
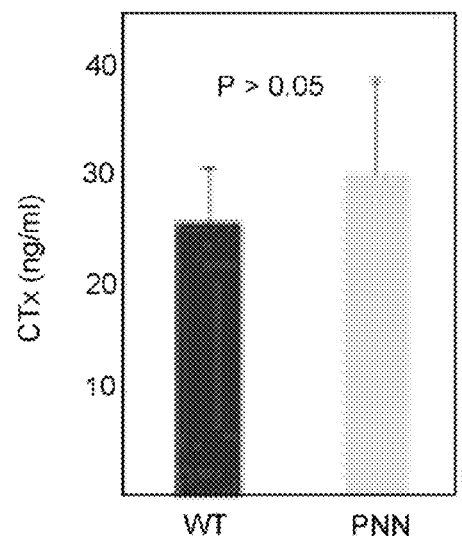

Next, the cellular basis for the high bone mass in PNN mice was examined. Staining for tartrate resistant acid phosphatase (TRAP) activity on tibia sections of mice at 8 weeks of age revealed that the mutants in fact had more osteoclasts per bone surface area than wild type littermates (FIGS. 3N, 3P, 3O, 3Q, and 3Y). Assays for in vivo osteoclast activity in serum samples revealed no significant differences between mutant and wild type littermates (FIG. 3Z). On the other hand, calcein double-labeling experiments indicated that whereas the mineral deposition rate as indicated by the distance between the double labels was not significantly altered in either the trabecular (FIGS. 3T and 3U) or the cortical bone (FIGS. 3V and 3W), PNN mutants exhibited a marked increase in the number of double-labeled surfaces within the trabecular bone (FIGS. 3R, 3S, and 3X). Thus, the increase of bone mass in PNN animals was unlikely to be due to defects in osteoclasts or upregulation of osteoblast activity, but rather was due to an increase in the number of active osteoblasts.

Example 4

Notch Signaling is Critical for Embryonic Skeletal Development

Figure 5Q:
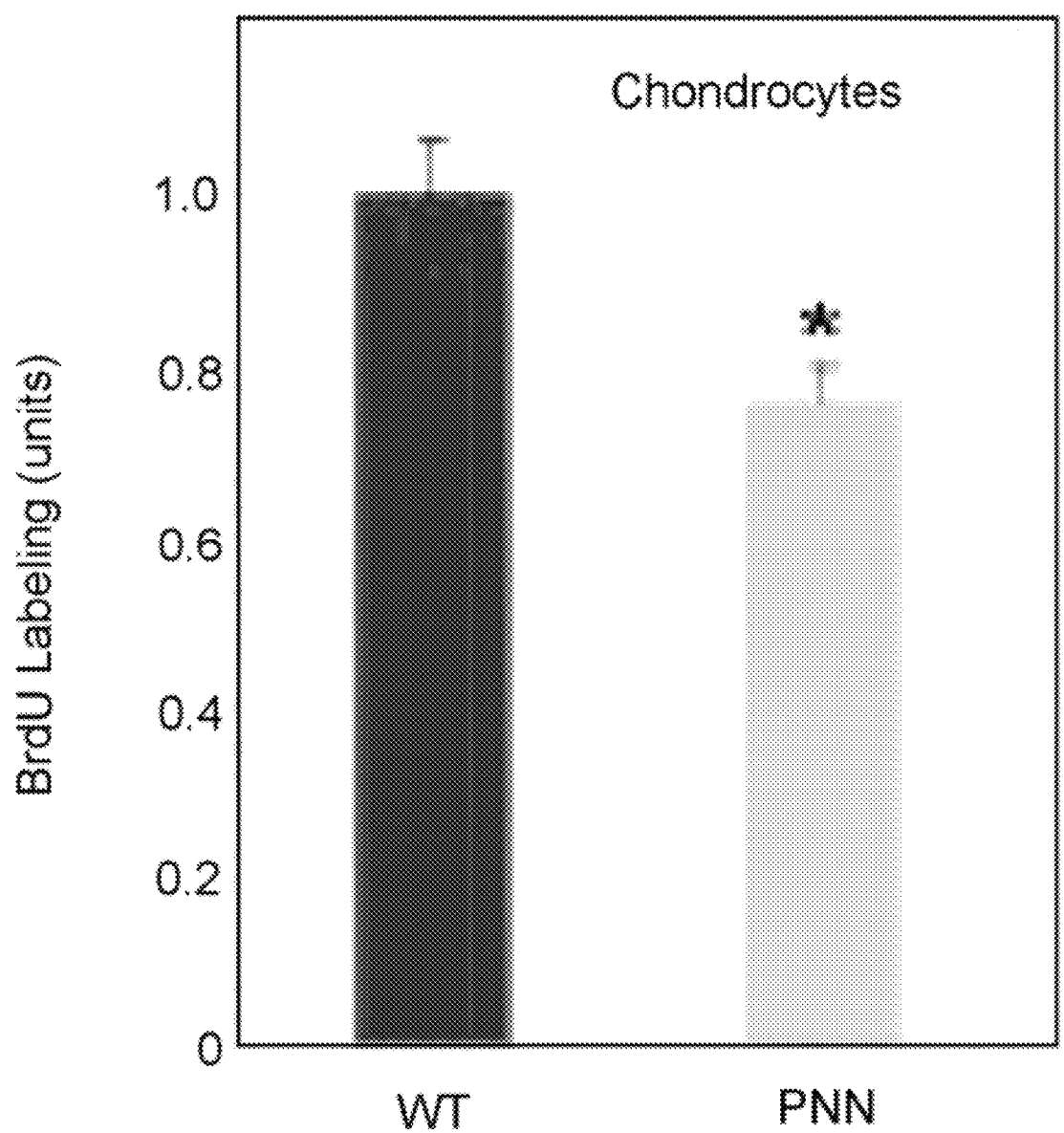
FIG. 5 demonstrates molecular and histological analyses in PNN and wild type (WT) embryos. In situ hybridization was done on adjacent longitudinal sections through the tibia from E18.5 littermates (FIG. 5A-5C, 5G-5I, 5E-5F, 5K-5L). (Double-headed arrows denote length of expression domain; yellow contours demarcate chondro-osseous junction; arrows indicate last low of hypertrophic chondrocytes)
FIGS. 5D and 5J show H&E staining of medial longitudinal sections through the tibia of E18.5 littermates. Boxed regions are shown at high magnification as insets. Black arrowheads denote marrow cells. (Double-headed arrows: length of hypertrophic zone) Ihh in situ hybridization was done on adjacent longitudinal sections through the tibia from E14.5 littermates (FIGS. 5M-5O and 5R-5T). Yellow arrowheads denote major expression domains of Ihh. (Double-headed arrows: lengths of expression domains)
FIGS. 5P and 5U show H&E staining of medial longitudinal sections through the tibia of E14.5 littermates. (Double-headed arrows: length of hypertrophic zone) FIGS. 5Q and 5V graphically illustrate the relative BrdU labeling index in E18.5 littermates (*: $p<0.05$; $n=3$).
Figure 5V:
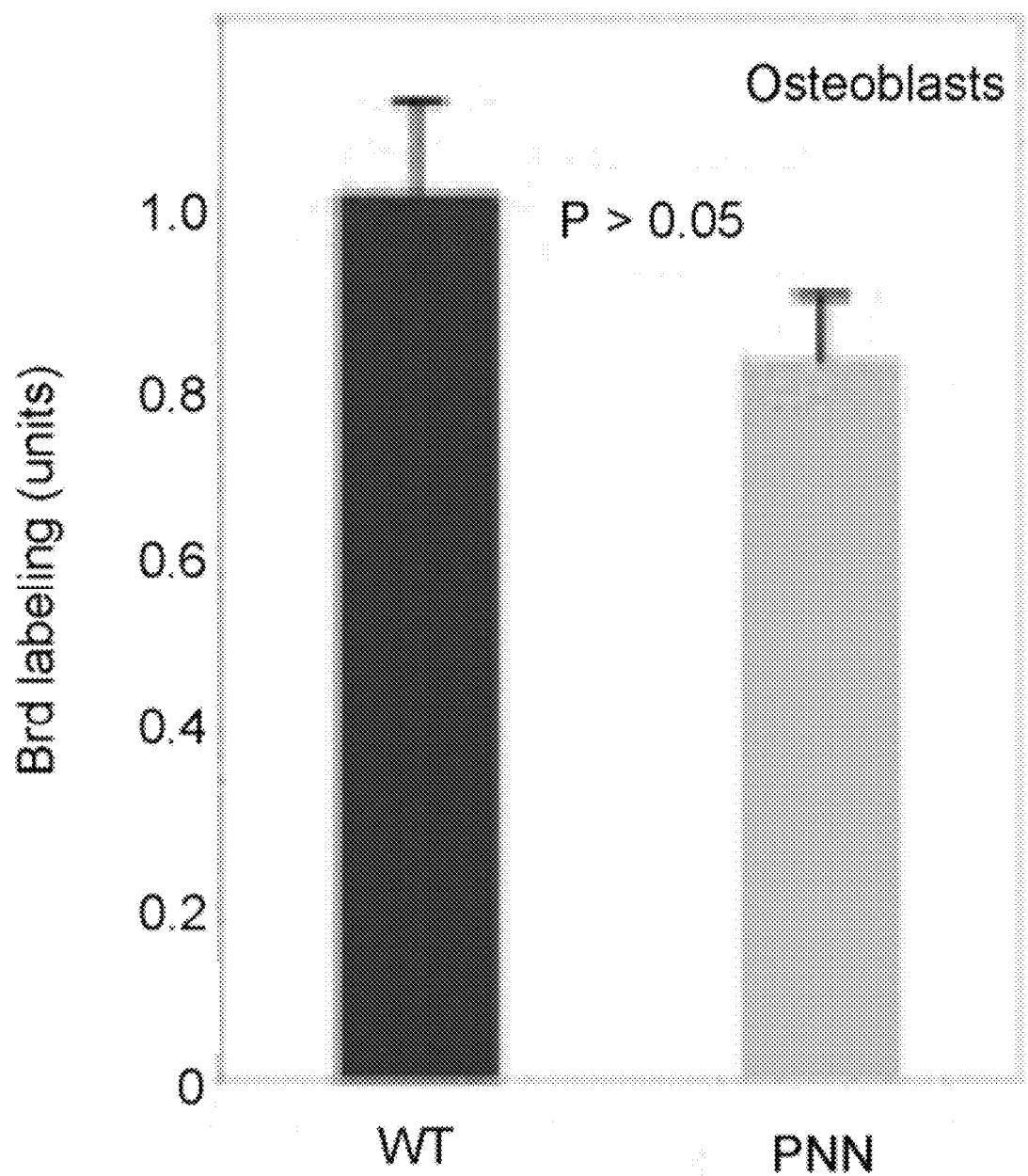

To determine the developmental onset of the skeletal phenotypes, PPS and PNN embryos were analyzed. At E18.5, histology revealed that elongation of hypertrophic cartilage and increase in osteoblast number within the marrow region was already evident in the mutant embryos (PPS, FIG. 4; PNN, FIGS. 5D and 5J). The increased osteoblast population in mutant embryos expressed high levels of bone sialoprotein (BSP) (FIG. 5K), as well as type I collagen (Col$\alpha$1(I)) and alkaline phosphatas (AP) (data not shown). Interestingly, the number of osteoclasts expressing TRAP appeared to be increased within the trabecular region of PNN mutants (FIGS. 5F and 5L). Moreover, the excessive number of trabecular osteoblasts in PNN mutants did not reflect changes in cell proliferation, as BrdU labeling experiments indicated no increase in the labeling index among mutant trabecular osteoblasts (FIG. 5V). Similarly, immunohistochemistry with an antibody specific for activated caspase 3 detected no differences in apoptosis of trabecular osteoblasts between mutant and wild type animals (data not shown). Thus, genetic disruption of Notch signaling from the limb mesenchyme results in elongation of the hypertrophic cartilage, as well as overproduction of trabecular osteoblasts, in embryonic long bones.

To further characterize the cartilage defect, molecular analyses on sections of embryonic tibia were performed. At E18.5, the hypertrophic zone expressing Col$\alpha$1(X) was significantly longer in PPS (FIG. 4) or PNN mutants (FIGS. 5B and 5H) than in wild type littermates. Indian hedgehog (Ihh), normally restricted to the prehypertrophic/early hypertrophic region at this stage, persisted at a lower level throughout much of the mutant hypertrophic zone (FIGS. 5A and 5G). Matrix metalloproteinase 13 (MMP13), normally expressed at high levels in a single row of terminal hypertrophic chondrocytes, was activated in the mutant at a lower level in many rows of hypertrophic cells before eventually reaching the high level (FIGS. 5C and 5I). In addition, in vivo BrdU labeling experiments revealed a 25% reduction in the labeling index of growth plate chondrocytes in PNN mutants versus wild type littermates (FIG. 5Q). At E14.5, both histology (FIGS. 5P and 5U) and the expression profile of Col$\alpha$1(X) (FIGS. 5N and 5S) indicated that the hypertrophic region was significantly reduced in PNN mutants. The two major Ihh-expressing domains were less well separated (FIGS. 5M and 5R), and the number of terminal hypotrophic chondrocytes expressing MMP13 was markedly reduced in PNN mutants (FIGS. 5O and 5T). Thus, Notch signaling in the growth plate positively controls the proliferation of nonhypertrophic chondrocytes, the onset of chondrocyte hypertrophy and also subsequent progression toward terminal hypertrophy.

To determine the relative importance of Notch1 versus Notch2 in the developing skeleton, the phenotypes of E18.5 embryos carrying different allelic combinations were compared. In embryos missing both Notch1 alleles and one Notch2 allele (Pre1Cre; N1$^{c/c}$; N2$^{c/+}$), the bone marrow appeared indistinguishable from the wild type (FIGS. 6B and 6D) although the hypertrophic zone was slightly elongated (FIGS. 6A and 6C). On the other hand, embryos missing both Notch2 alleles and one Notch1 allele (Pre1Cre; N1$^{c/+}$; N2$^{c/c}$) exhibited excessive osteoblasts in the marrow region (FIG. 6F) and a marked elongation of the hypertrophic zone (FIG. 6E). In fact, the bone marrow phenotype here was indistinguishable from that in the mutant missing all copies of Notch1 and Notch2 (Pre1Cre; N1$^{c/c}$; N2$^{c/c}$) (FIG. 6H), although the hypertrophic zone was further expanded upon deletion of the remaining Notch1 allele (FIG. 6G). Thus, Notch2 appeared to be the predominant regulator for both chondrocyte maturation and osteoblast formation, but Notch1 also plays a role in chondrocyte maturation.

Example 5

No Obvious Phenotype with Removal of Notch1 and Notch2 in Committed Osteoblasts

Figure 7G:
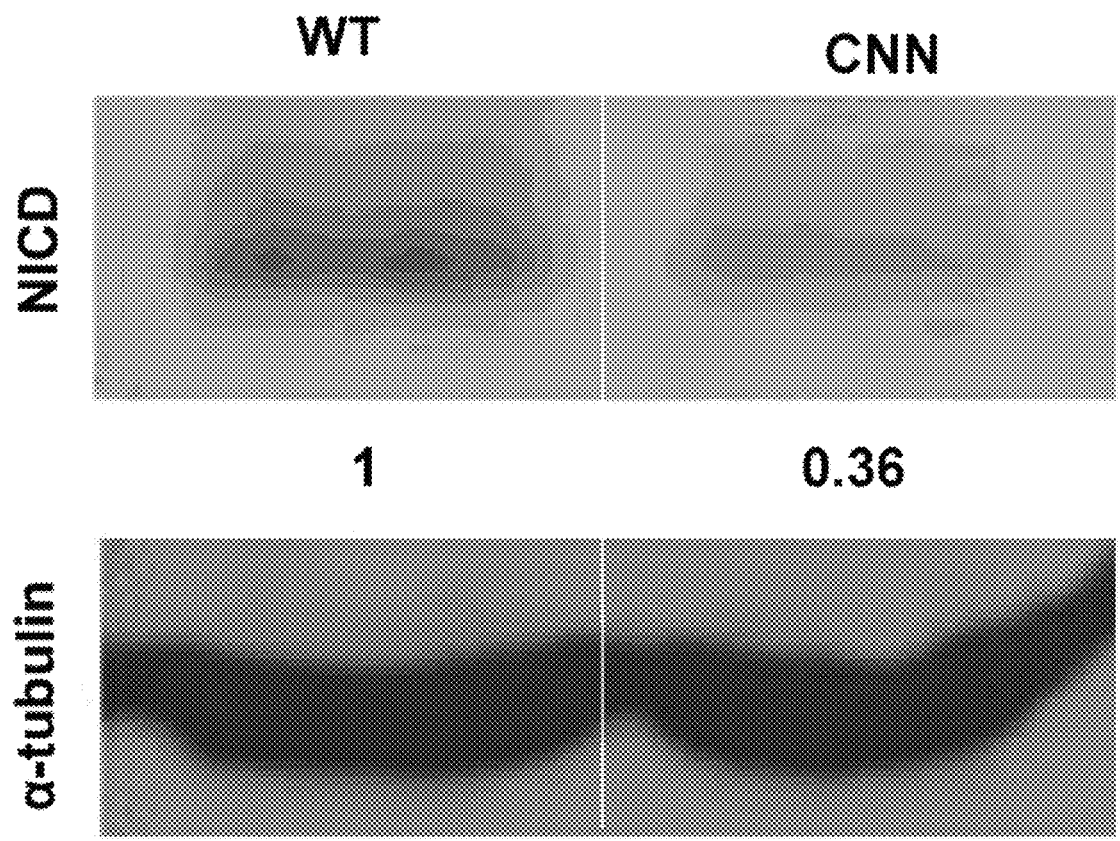
FIG. 7 demonstrates the lack of obvious skeletal phenotype in CNN mice at 8 weeks of age.
FIGS. 7A and 7B show X-ray radiographs of hindlimbs from littermates. Double-headed arrows denote the length of the tibias. Arrowheads point to the trabecular bone regions.
FIGS. 7C and 7D show medial longitudinal sections through 3-D reconstructions of the tibia by μCT.
FIGS. 7E and 7F show H&E staining of medial longitudinal sections through the tibia. Green arrows denote bone marrow; and red arrows point to the growth plate. Western blot protein analyses for NICD in primary osteoblasts is shown in FIG. 7G. The signal intensity was normalized to α-tubulin.

To investigate whether Notch signaling is required in committed osteoblasts, we ablated Notch1 and Notch2 using Coll-Cre, which expresses Cre under the control of a 2.3-kb promoter sequence of the murine Col$\alpha$1(I) gene and was previously shown to function effectively in these cells. Animals missing all alleles of Notch1 and Notch2 in osteoblasts (Coll-Cre; N1$^{n/c}$; N2$^{c/c}$, hereafter CNN mutants) were viable and, in contrast to PPS and PNN mutants, showed no obvious skeletal phenotype at 8 weeks of age by X-ray radiography, μCT analyses, and histology (FIG. 7). The efficacy of Coll-Cre was confirmed by the significant reduction of NICD levels in primary osteoblasts isolated from CNN mutants (FIG. 7). Thus, unlike the impact in osteoblast progenitors, removal of Notch1 and Notch2 from committed osteoblasts does not significantly affect trabecular bone formation.

Example 6

Notch Regulation of Bone Marrow Mesenchymal Progenitors

Figure 8A:
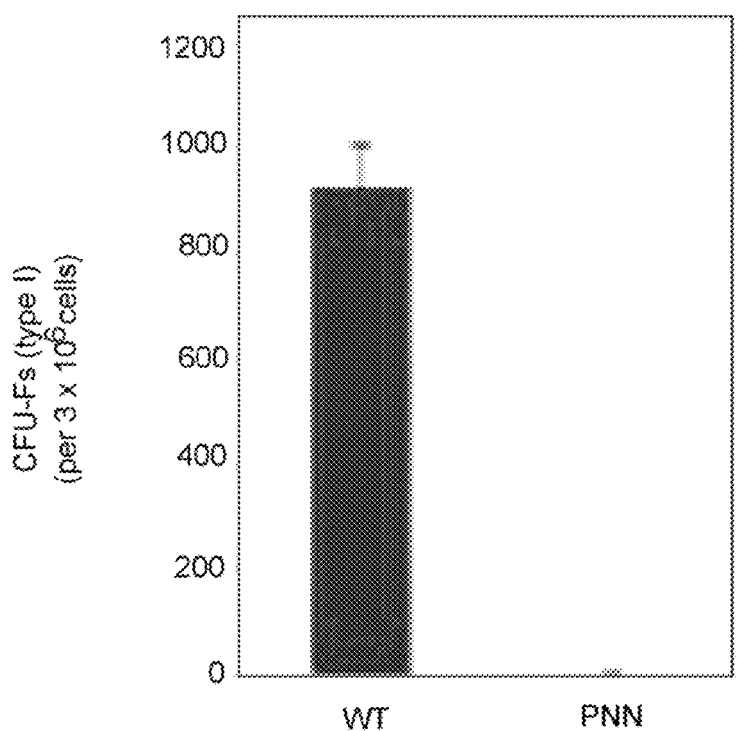
FIG. 8A shows bone marrow CFU-F assays for wild type (WT) versus PNN mutant littermates.

The finding that Notch removal in mesenchymal progenitors but not in committed osteoblasts dramatically altered trabecular bone formation, and the increase in osteoblast number without changes in cell death or proliferation, prompted an examination of whether fate allocation of bone marrow mesenchymal progenitors was affected in PNN mutants. Mesenchymal progenitors are found in the clonogenic subset of adherent bone marrow stromal cells (BM-SCs), known as colony-forming unit-fibroblasts (CFU-Fs), and are capable of forming multiple mesenchymal cell types in vitro. Moreover, a subset of mesenchymal progenitors are believed to be stem cells, whose clonal progenies expanded in vitro can generate all cell types associated with the bone marrow upon in vivo transplantation. To approximate the size of the progenitor pool, we cultured BMSCs at low density to assay for the frequency of CFU-Fs in the marrow of mutant versus wild type littermate postnatal animals. Remarkably, although a similar number of total marrow cells were retrieved from the PNN mutant and wild type bones, the mutant marrow contained hardly any "type I" (see Methods) CFU-Fs (0-1 per $10^6$ marrow cells), whereas wild type samples typically contained hundreds of them per $10^6$ marrow cells in such assay (FIG. 8A). In addition, the mutant samples formed significantly fewer (~5 per $10^6$ marrow cells) and smaller (fewer cells within each cluster, data not shown) "type II" CFU-Fs than the wild type (~20 per $10^6$ marrow cells). Thus, removal of Notch signaling from limb mesenchymal progenitors results in a severe reduction in the number of mesenchymal progenitors in postnatal bone marrow.

Figure 8B:
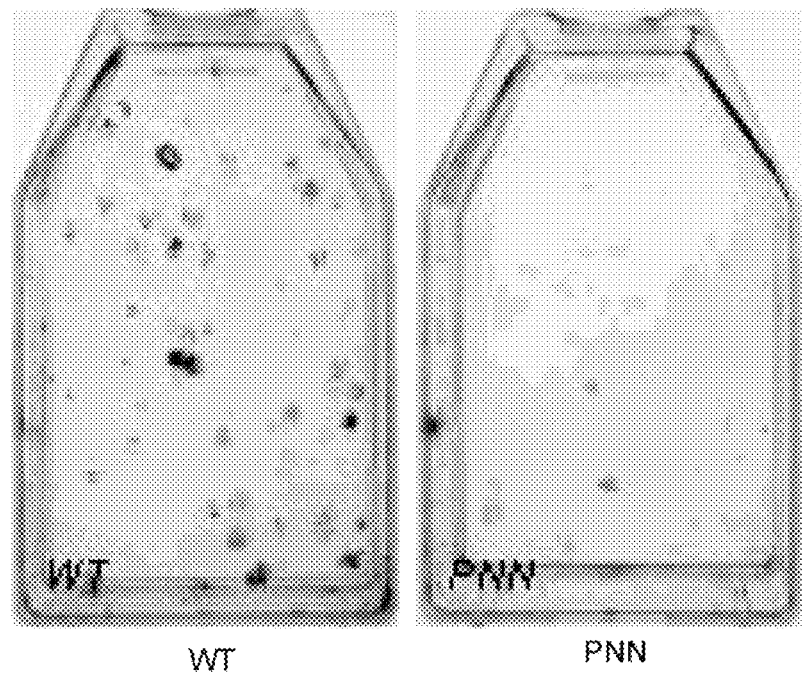
FIG. 8B depicts AP staining after 8 days in osteogenic medium following CFU-F assays.
Figure 8C:
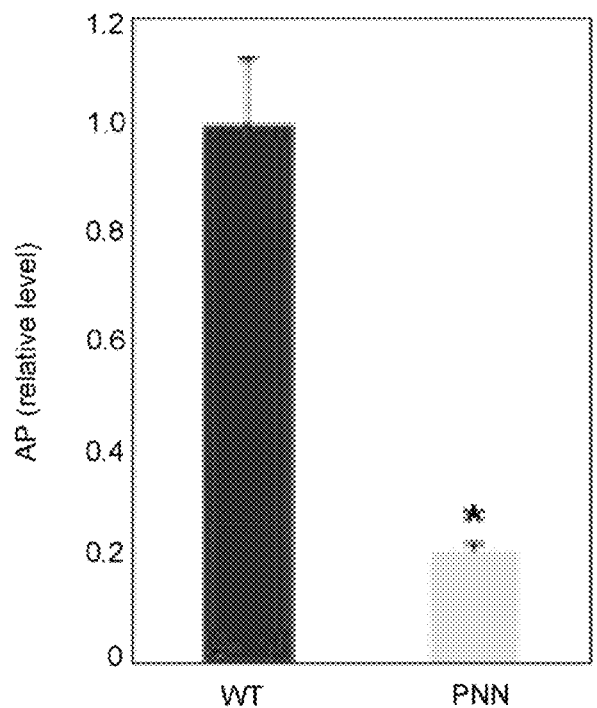
FIG. 8C illustrates AP quantitative assay for high-density BMSCs cultures in osteogenic medium.
Figure 8D:
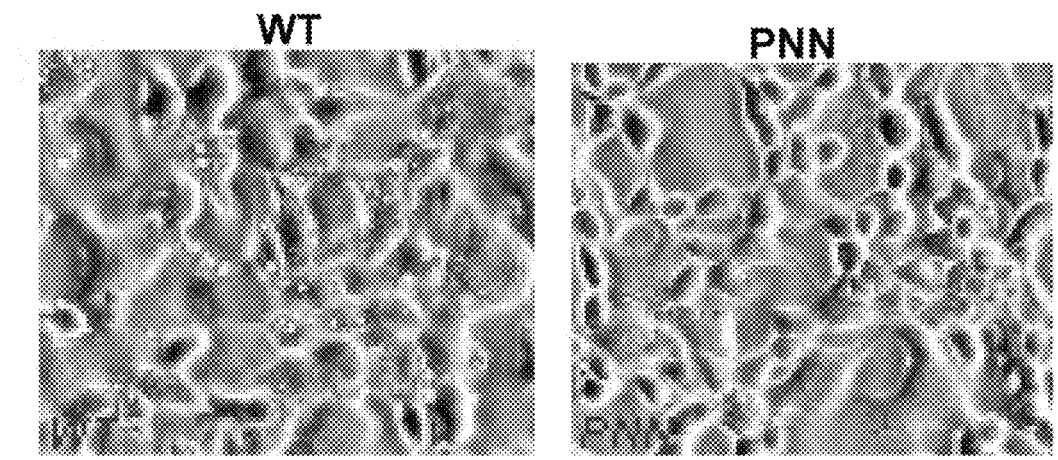
FIG. 8D is phase-contrast pictures of high-density BMSCs cultured in adipogenic medium. Note the lipid droplets in wild type cells.
Figure 8F:
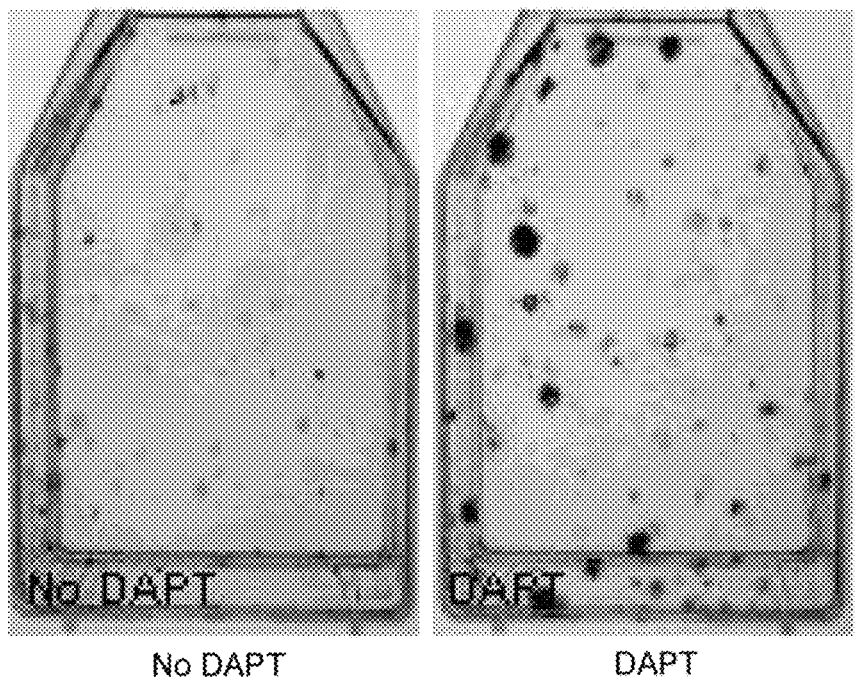
FIG. 8F shows AP staining immediately following CFU-F assays.

The differentiation capacity of BMSCs isolated from mutant versus wild type mice was assessed. When cultured in osteogenic media following formation of CFU-Fs, the PNN mutant samples produced much fewer osteoblast-lineage cells (AP-positive) than the wild type (FIG. 8B). Similarly, when cultured at a high density under osteogenic or adipogenic conditions, the mutant BMSCs produced little AP activity (FIG. 8D), or virtually no adipocytes containing lipid droplets (FIGS. 8E and 8F), respectively. Thus, consistent with the loss of mesenchymal progenitors, BMSCs isolated from Notch-deficient postnatal animals possessed little capacity to differentiate into mesenchymal cell types. These findings therefore support the notion that the progenitor population was "exhausted" in vivo by unchecked osteoblast differentiation.

Figure 8G:
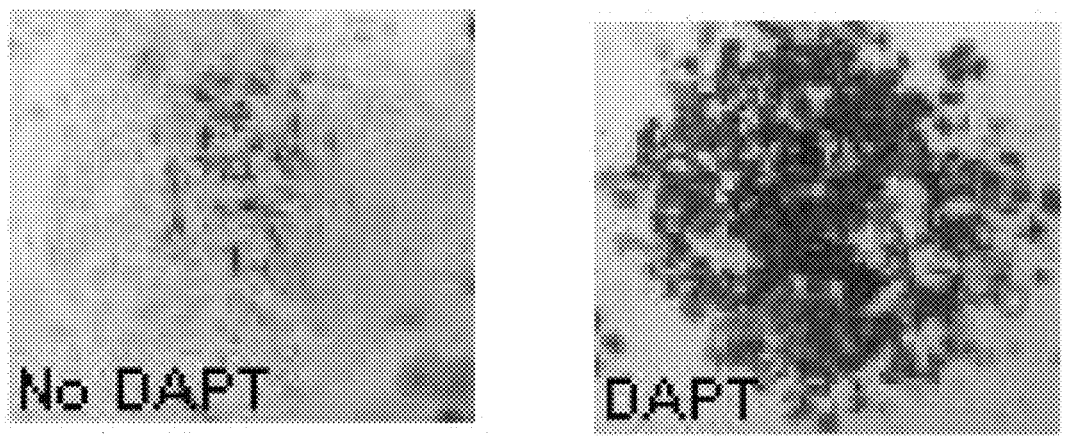
FIG. 8G is representative of "type II" CFU-Fs stained for AP.
Figure 8H:
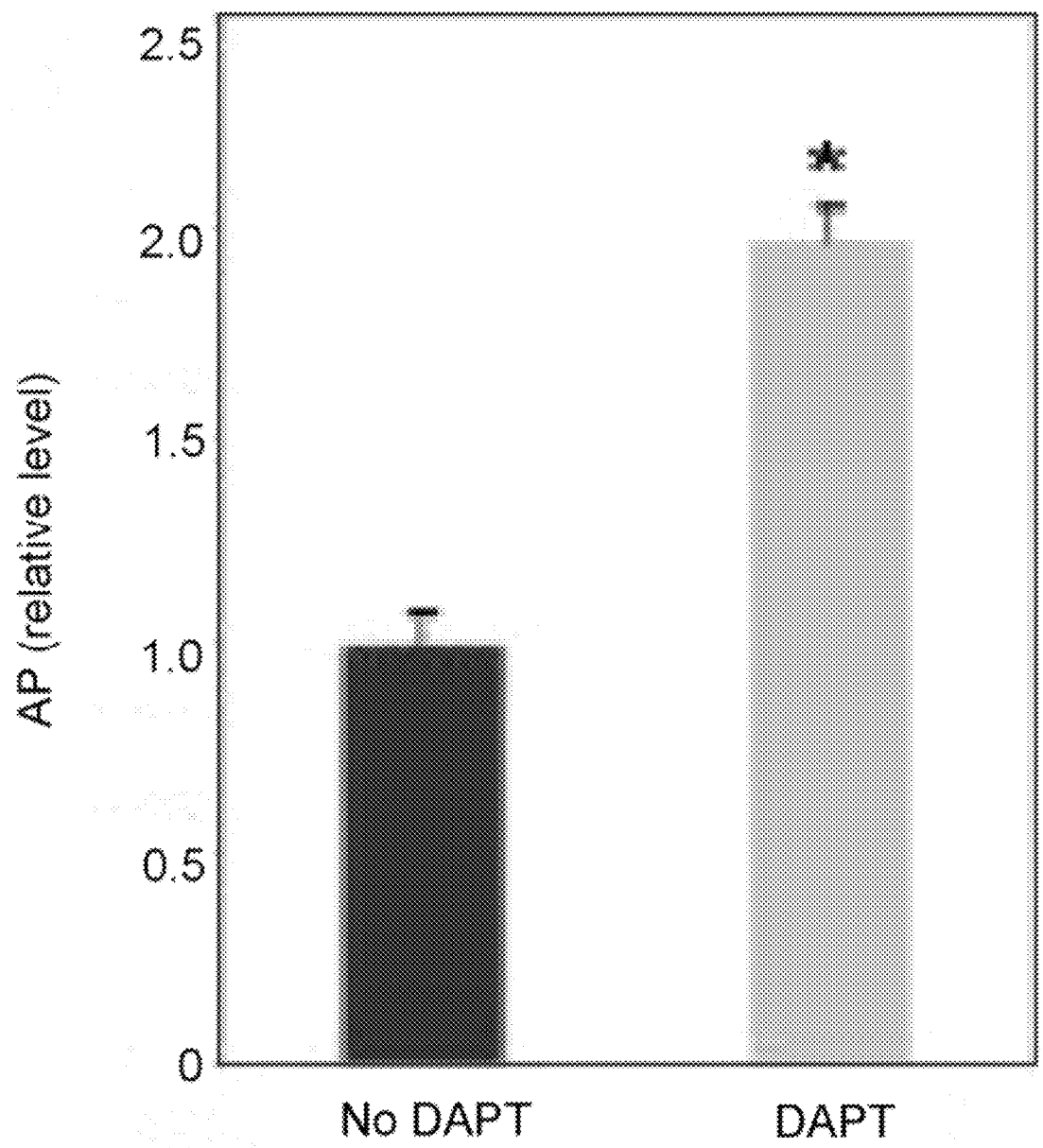
FIG. 8H illustrates an AP quantitative assay for high-density wild type BMSCs cultures in osteogenic medium with or without DAPT. (*: $p<0.05$).

It was also assessed whether Notch signaling could directly control bone marrow mesenchymal progenitors and their differentiation. Specifically, we assayed for the frequency of CFU-Fs in wild type BMSCs in the presence or absence of DAPT (N—[N-(3,5-Difluorophenacetyl)-L-alanyl]-S-phenylglycine t-butyl ester), a γ-secretase inhibitor that blocks Notch signaling. DAPT completely eliminated "type I" CFU-Fs (FIG. 8G-I), although it did not alter the number of "type II" CFU-Fs (~20 per 106 marrow cells). Interestingly, when assayed directly for AP activity without being further cultured in osteogenic conditions, nearly all "type II" CFU-Fs from the DAPT-treated samples stained strongly positive (FIG. 8K), with many containing only AP positive cells (FIGS. 8M and 8K), whereas in the non-treated samples the clusters contained only a small number of positive cells (FIGS. 8J and 8L). Similarly, when wild type BMSCs were cultured at a higher density under osteogenic conditions, DAPT significantly increased AP expression (FIG. 8N). Overall, these results support the notion that Notch signaling maintains the pool of mesenchymal progenitors and suppresses osteoblast differentiation.

The identity of cells activating Notch signaling in bone marrow mesenchymal progenitors in vivo is unknown. Likewise, it is not known whether CSL-mediated transcription is responsible for all Notch signaling in the skeleton, although several in vitro studies have implicated this mechanism in osteogenic cells. The present study indicates that suppressing Notch signaling in bone marrow mesenchymal progenitors may stimulate bone anabolism. In this regard, it should be noted that genetic removal of PS1 and PS2 in committed osteoblasts using Col1-Cre resulted in an increase in osteoclastogenesis in older mice (6 months). Thus, long-term inhibition of Notch signaling in the bone marrow environment may need to be coupled with additional means to curtail osteoclast production or activity to achieve desirable results. Alternatively, pulsatile application of Notch inhibition may avoid undesirable chronic effects. Finally, activating Notch signaling in bone marrow mesenchymal progenitors may help to maintain their phenotype and to expand their population in vitro.

Example 7

Notch-RBP-Jκ Negatively Regulates Bone Formation

Figure 9:
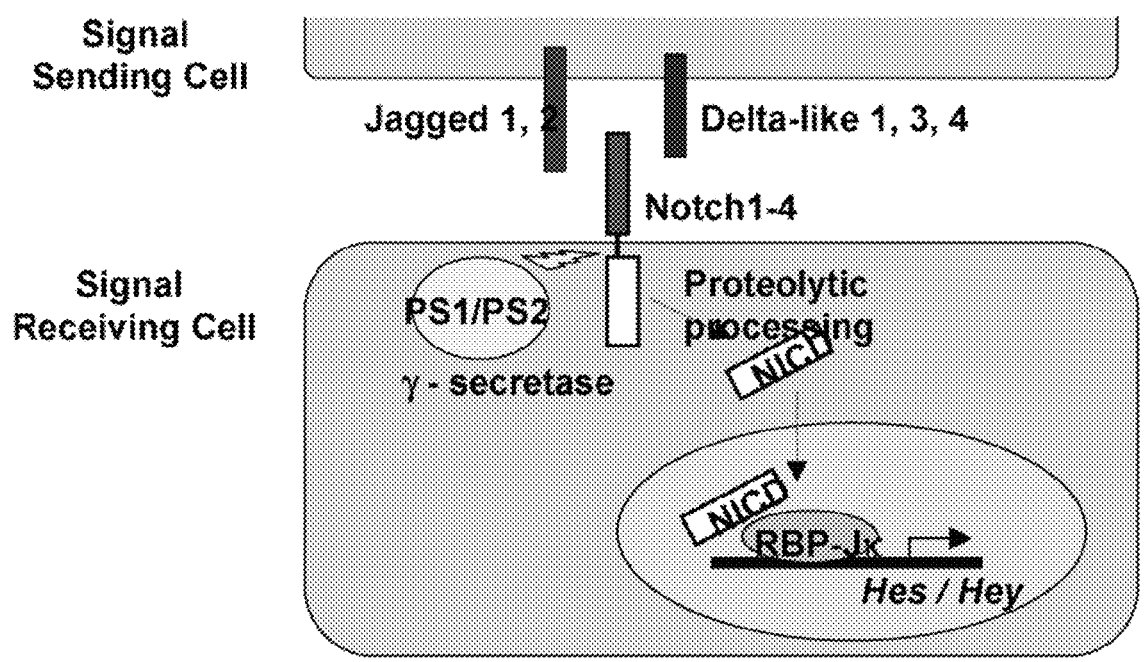
FIG. 9 depicts a schematic of canonical Notch signaling. Ligand binding triggers cleavage of Notch to NICD, which activates RBP-Jκ and upregulates Hes/Hey molecules.

Examples 1-6 establish that Notch signaling in the limb mesenchyme-lineage cells functions as a gatekeeper in osteoblast differentiation from mesenchymal progenitors, but the molecular mediators downstream of Notch receptors remain to be elucidated genetically. RBP-Jκ is an obligatory transducer of the canonical Notch signal, because it directly binds the Notch intracellular domain (NICD) and activates Hes/Hey target gene expression in the nucleus (FIG. 9). To determine whether Notch signaling in bone requires RBP-Jκ, the RBP-Jκ coding region was genetically removed from the embryonic limb skeletal precursor cells with Prx1-Cre to produce Prx1-cre; RBP-Jκ$^{f/f}$ mice. Removal of RBP-Jκ recapitulated the high-bone-mass phenotype observed in adolescent Notch-deficient mice (FIG. 10). These results therefore further establish that Notch-RBP-Jκ signaling negatively control bone formation.

What is claimed is:

1. A method for promoting osteogenesis in a subject, the method comprising (a) increasing the number of osteoblasts in a subject in need of osteogenesis by administering a Notch signaling inhibitor to the subject, and (b) detecting increased osteogenesis in the subject.

2. The method of claim 1, wherein the Notch signaling inhibitor is a gamma-secretase inhibitor.

3. The method of claim 2, wherein the gamma-secretase inhibitor is selected from the group consisting of a dipeptide class, sulfonamide class, transition state mimic class, benzodiazepine class, benzocaprolactam class gamma-secretase inhibitor, and combinations thereof.

4. The method of claim 1, wherein the Notch signaling inhibitor is a RBP-Jκ inhibitor.

5. The method of claim 1, wherein the Notch signaling inhibitor is selected from the group consisting of DAPT (N—[N-(3,5-Difluorophenacetyl-L-alanyl)]-S-phenylglycine t-Butyl Ester), 1-(S)-endo-N-(1,3,3)-Trimethylbicyclo[2.2.1]hept-2-yl)-4-fluorophenyl Sulfonamide, WPE-III31C, S-3-[N'-(3,5-difluorophenyl-alpha-hydroxyacetyl)-L-alanilyl]amino-2,3-dihydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one, and combinations thereof.

6. A method for treating a bone disorder, the method comprising (a) contacting a mammalian cell with a Notch signaling inhibitor such that the mammalian cell differentiates into a cell of an osteoblast lineage, (b) detecting increased osteogenesis in the subject, wherein the increased osteogenesis treats the bone disorder.

7. The method of claim 6, wherein the Notch signaling inhibitor is a gamma-secretase inhibitor.

8. The method of claim 7, wherein the gamma-secretase inhibitor is selected from the group consisting of a dipeptide class, sulfonamide class, transition state mimic class, benzodiazepine class, benzocaprolactam class gamma-secretase inhibitor, and combinations thereof.

9. The method of claim 6, wherein the Notch signaling inhibitor is a RBP-Jκ inhibitor.

10. The method of claim 6, wherein the Notch signaling inhibitor is selected from the group consisting of DAPT (N—[N-(3,5-Difluorophenacetyl-L-alanyl)]-S-phenylglycine t-Butyl Ester), 1-(S)-endo-N-(1,3,3)-Trimethylbicyclo[2.2.1]hept-2-yl)-4-fluorophenyl Sulfonamide, WPE-III31C, S-3-[N'-(3,5-difluorophenyl-alpha-hydroxyacetyl)-L-alanilyl]amino-2,3-dihydro-1-methyl-5-phenyl-1H-1,4-benzodiazepin-2-one, (N)-[(S)-2-hydroxy-3-methyl-butyryl]-1-(L-alaninyl)-(S)-1-amino-3-methyl-4,5,6,7-tetrahydro-2H-3-benzazepin-2-one, and combinations thereof.

11. A method for increasing osteoblast number in a subject, the method comprising (a) identifying a subject in need of increased numbers of osteoblast cells, (b) administering a Notch signaling inhibitor to the subject, and (c) detecting the increased osteoblast number in the subject.

12. A method for increasing trabecular bone growth in a subject, the method comprising (a) identifying a subject in need of increased trabecular bone growth, (b) administering a Notch signaling inhibitor to the subject, and (c) detecting the increased trabecular bone growth in the subject.

* * * * *